United States Patent
Tanaka et al.

(10) Patent No.: US 7,335,881 B2
(45) Date of Patent: Feb. 26, 2008

(54) METHOD OF MEASURING DIMENSIONS OF PATTERN

(75) Inventors: Maki Tanaka, Yokohama (JP); Chie Shishido, Yokohama (JP); Yuji Takagi, Kamakura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 402 days.

(21) Appl. No.: 11/019,995

(22) Filed: Dec. 23, 2004

(65) Prior Publication Data

US 2005/0173633 A1    Aug. 11, 2005

(30) Foreign Application Priority Data

Dec. 26, 2003    (JP)    ............... 2003-432012

(51) Int. Cl.
*H01L 21/02* (2006.01)
*G01B 15/00* (2006.01)

(52) U.S. Cl. ...................... 250/311; 250/310
(58) Field of Classification Search ........... 250/307
See application file for complete search history.

(56) References Cited

U.S. PATENT DOCUMENTS 6,879,392 B2 * 4/2005 Sakai et al. ............ 356/237.4
6,909,930 B2 * 6/2005 Shishido et al. ............ 700/121
7,098,456 B1 * 8/2006 Lorusso et al. ............ 250/310

FOREIGN PATENT DOCUMENTS

JP    2003-173948    6/2006

* cited by examiner

*Primary Examiner*—Nikita Wells
*Assistant Examiner*—James J Leybourne
(74) *Attorney, Agent, or Firm*—Antonelli, Terry, Stout & Kraus, LLP.

(57) ABSTRACT

With complexity of a process, the setting of conditions for pattern measurement by an SEM image falls into difficulties. However, the present invention aims to realize the setting of easy and reliable measuring conditions even with respect to a pattern complex in structure. Points characterized in terms of an SEM image signal are calculated as candidates for measurement values. The calculated candidates for measurement values are displayed with being superimposed on the SEM image. An operator selects the optimum one from the displayed candidates and thereby determines the optimum image processing condition for measurement. The relationship between the result of measurement under a predetermined image processing condition and pattern portions has been made clear using model data of a sectional shape and an electron beam simulation image.

18 Claims, 27 Drawing Sheets

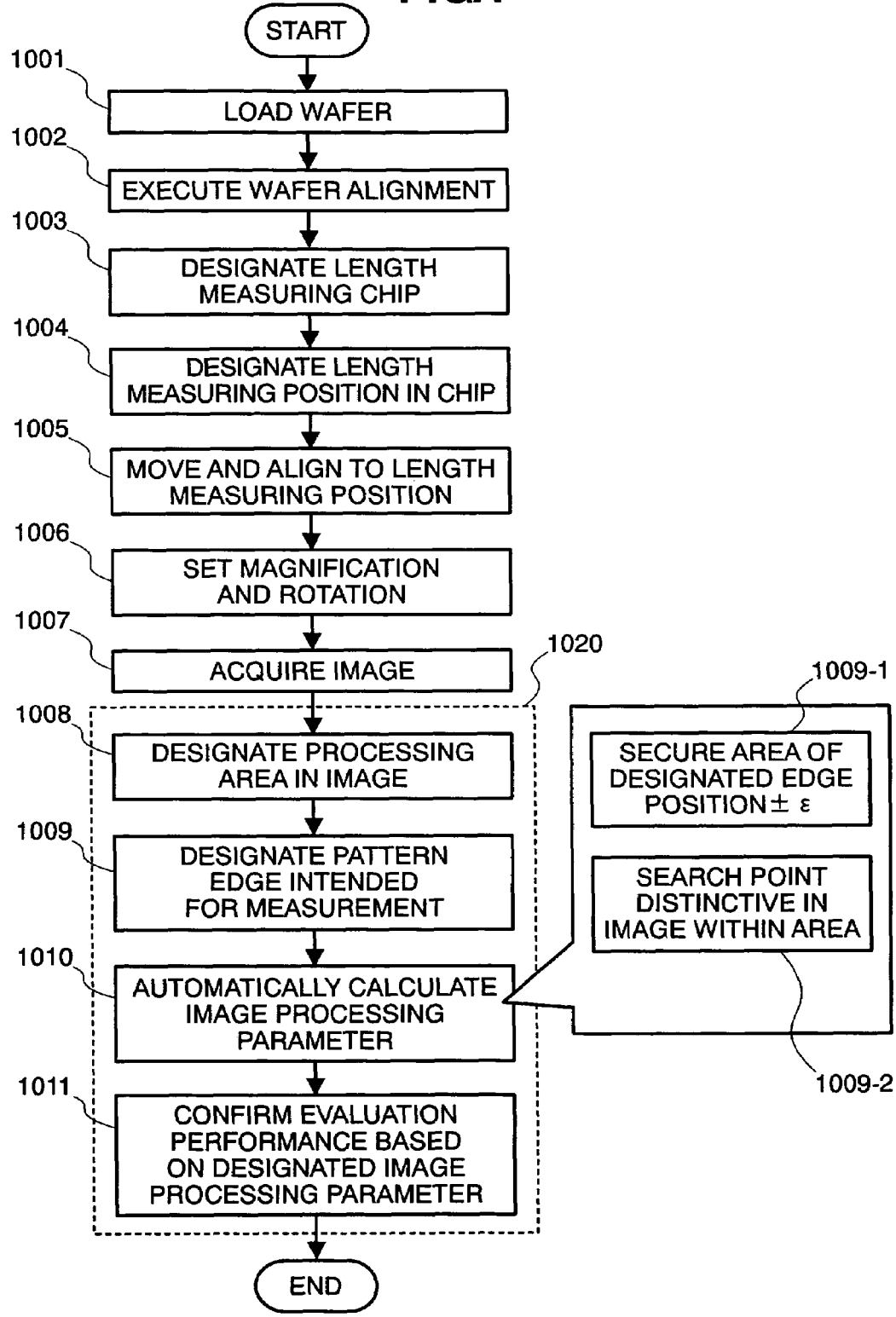

MAXIMUM TILT POINTS AT RESPECTIVE SLOPES

DIMENSION $th = min + (max-min) \times a$
$a$ : PREDETERMINED RATIO

DIMENSION

SLOPE LINE
EDGE
BASE LINE
DIMENSION

FIG.3(a)
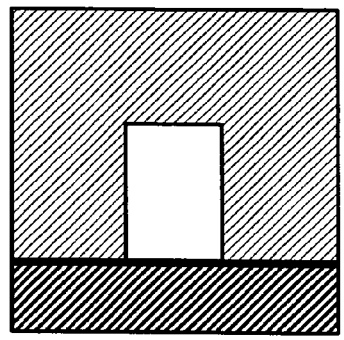
FIG.3(b)
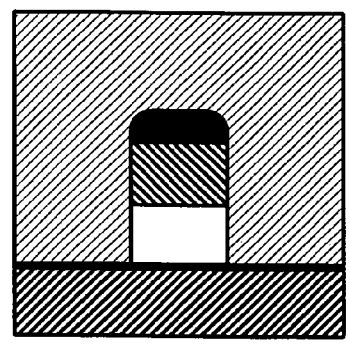
FIG.3(c)
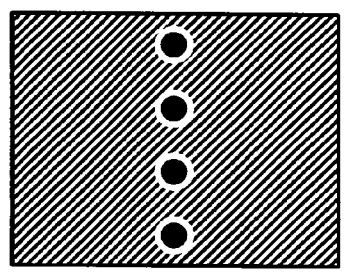
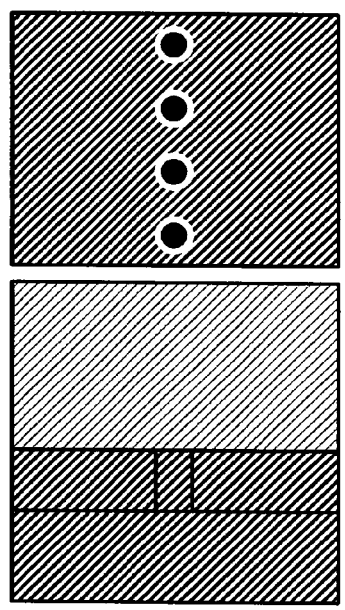
FIG.3(d)
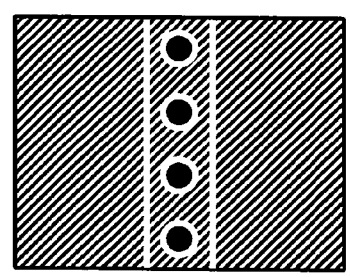
FIG.3(e)
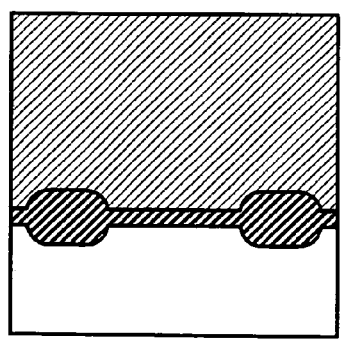
FIG.3(f)
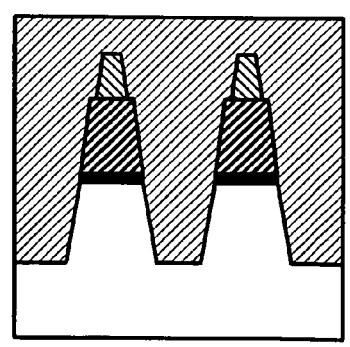

STEP 1007

400 SELECTION RANGE

STEP 1008

401 MEASURING TARGET POSITION

400 SELECTION RANGE

STEP 1009

4001 DETERMINE

NG 4002

403 PULLDOWN MENUE

ALL
ALL
+ #1
× #2

402 MEASURED RESULT MARKS

FIG.6(a)
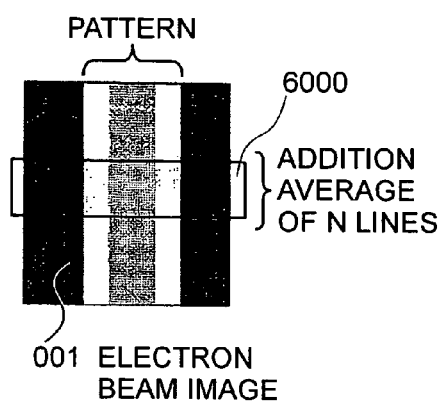
PATTERN
6000
ADDITION AVERAGE OF N LINES
001 ELECTRON BEAM IMAGE
FIG.6(b)
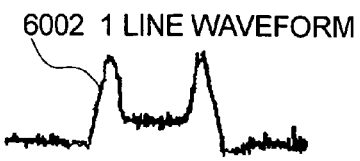
6002 1 LINE WAVEFORM
FIG.6(c)
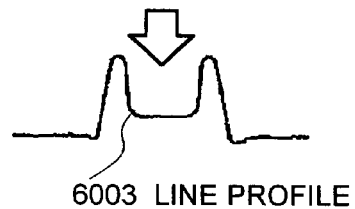
6003 LINE PROFILE
FIG.6(d)
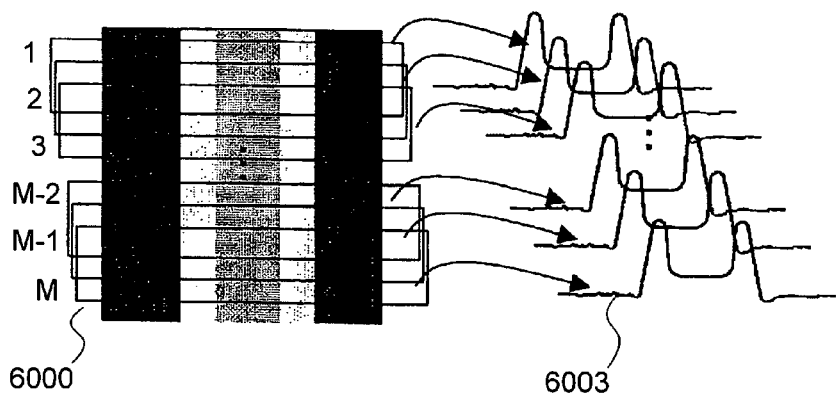
6000  6003
FIG.6(e)
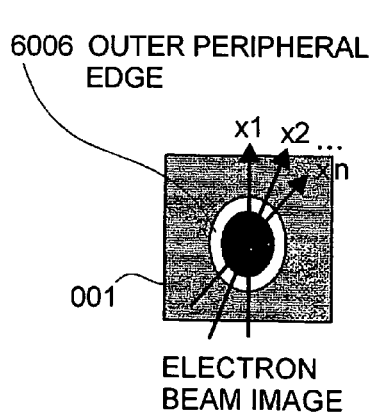
6006 OUTER PERIPHERAL EDGE
001 ELECTRON BEAM IMAGE
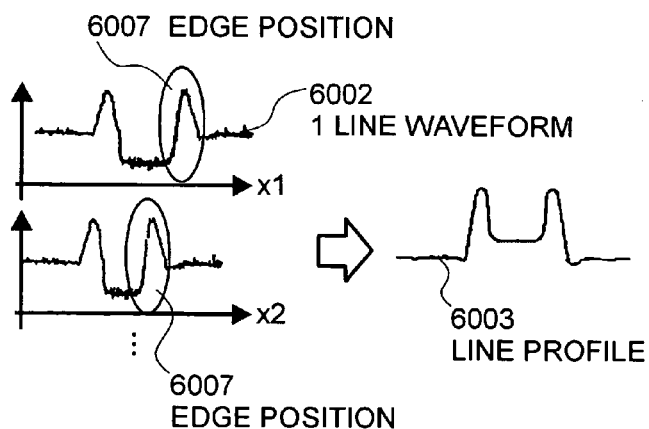
6007 EDGE POSITION
6002 1 LINE WAVEFORM
6007 EDGE POSITION
6003 LINE PROFILE

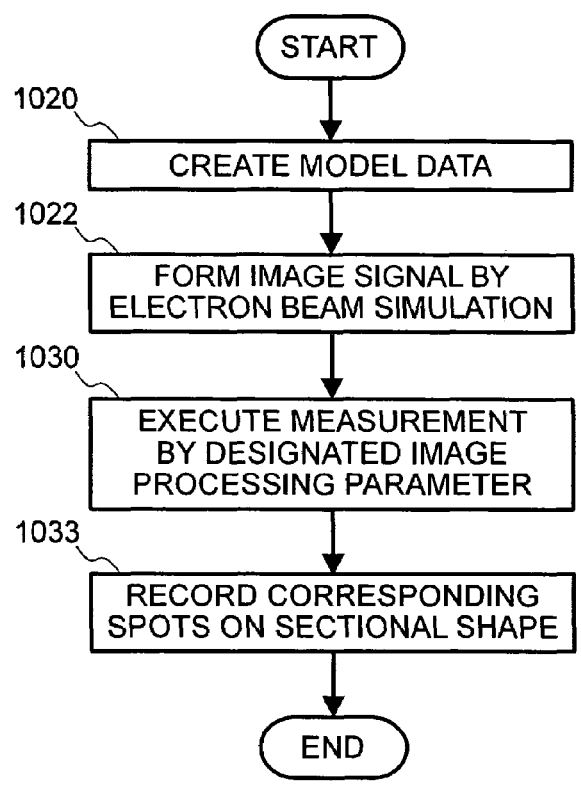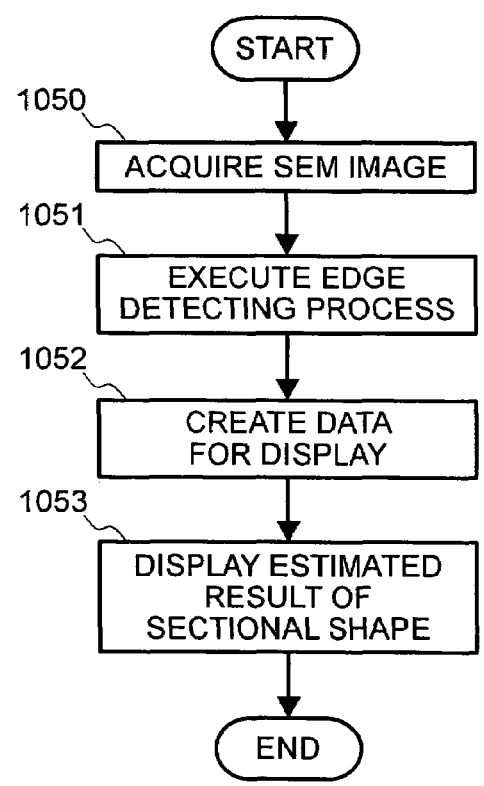

FIG.23(a)     FIG.23(b)
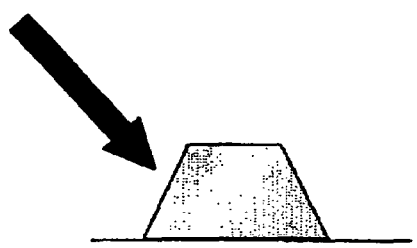 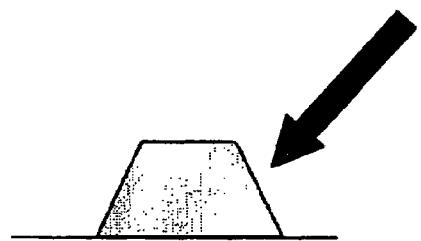
 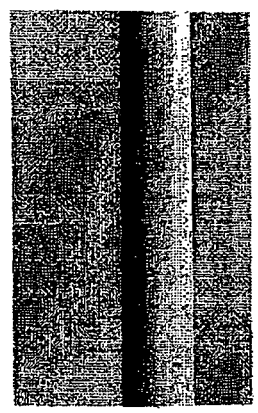   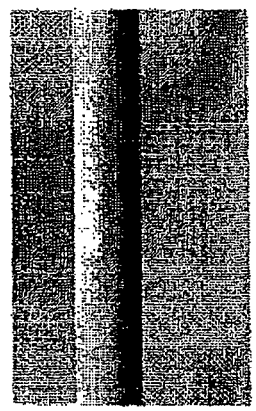 

| ELEMENT | SHAPE | MEASURED TARGET/RESULT | | IMAGE PROCESSING CONDITION |
|---|---|---|---|---|
| A | TRAPEZOID | 1. HEIGHT | FIXED(**nm) | |
| | | 2. UPPER SIDE | MEASURED RESULT | ① |
| | | 3. LOWER SIDE | MEASURED RESULT | ② |
| B | TRAPEZOID | 1. HEIGHT | FIXED(**nm) | |
| ⋮ | ⋮ | ⋮ | ⋮ | ⋮ |
| D | TRAPEZOID | | | |

METHOD OF MEASURING DIMENSIONS OF PATTERN

BACKGROUND OF THE INVENTION

The present invention relates to a method for processing an image obtained by imaging a pattern to thereby measure dimensions of the pattern, and particularly to a pattern measuring method suitable for evaluating, using an electron beam image of a circuit pattern, whether a processed form of the circuit pattern formed on a wafer in a semiconductor manufacturing process is good or not.

Nowadays, measurement and management of pattern dimensions using a critical dimension scanning electron microscope (length measuring SEM) dedicated to measurement is generally being performed in a semiconductor manufacturing process. The measurement of the pattern dimensions is automated by effecting an image processing technique on an acquired length measuring SEM image. Consequentially, operator's skill becomes unnecessary and variations in measurement due to differences among individuals have also been reduced. Such pattern measurement based on image processing is mainly intended for a single-layer pattern such as a resist, an insulating film, polysilicon or the like. There was also so much to make up, as shapes, relatively simple ones such as a circular form, wiring, etc.

FIGS. 2A, 2B and 2C show an example illustrative of measuring techniques. An image signal of an SEM changes according to the shape and material of a pattern and brightly glows at each edge portion of the pattern in particular. FIGS. 2A through 2C illustrates a processed example of a signal waveform indicative of a wiring shape pattern. In the signal waveform in the figures, two peaks (2011 and 2012) large in signal amount are equivalent to edge portions of a wiring. The positions of such edge portions are determined by such techniques as shown in FIGS. 2A through 2C so that the dimensions of the target pattern may be measured. The technique shown in FIG. 2A is a method (maximum gradient method) for detecting a maximum tilt position of each peak, the technique shown in FIG. 2B is a threshold method for detecting an edge position at a predetermined threshold value, and the technique shown in FIG. 2C is a linear approximate method for applying straight lines to each edge portion and a base material portion and detecting points of intersection of these.

In the pattern shown in FIGS. 2A through 2C, the peaks of the signal waveform are formed such that only one peak exists with respect to one edge. Therefore, the pattern dimensions could be measured with relative ease by such a method. With a change in recent semiconductor manufacturing techniques, however, the structure of a gate electrode is in the process of changing from such a conventional single-layer structure as shown in FIG. 3A to a multilayer film structure as in the case of a polysilicide gate or polymetal gate shown in FIG. 3B. Also the structure of device isolation changes from such a relatively simple LOCOS (Local Oxidization of Si) structure as shown in FIG. 3E to such Shallow Trench Isolation (hereinafter called "STI": device isolation) as shown in FIG. 3F. Further, for example, such a dual damascene structure as shown in FIG. 3D in which connecting viaholes shown in FIG. 3C are simultaneously formed, also appear in a wiring process. Ones complex in shape and material is on the increase. Therefore, samples each hard to cope with such a waveform that the signal waveform corresponding to each side face of the pattern has only the single peak such as shown in FIG. 2 is on the increase.

FIGS. 4A, 4B and 4C typically shows an SEM image of an STI pattern similar to FIG. 3E. FIG. 4A is a sectional typical view, FIG. 4B is an example of an image, and FIG. 4C is a waveform of FIG. 4B. As shown in FIGS. 4A through 4C, the waveform of a sample having such complex structure and shape has a plurality of peaks adjacent to one another. Such a measuring method as shown in FIG. 2 does not often obtain a proper result. A method for designating peaks to edges having such plural peaks respectively to perform edge detection, etc. have been disclosed in, for example, Japanese Patent Laid-open Nos. 2003-173948 and 2003-243291.

As shown in FIGS. 4A through 4C, the SEM signal waveform becomes complex in the pattern complex in shape. It is difficult to stably measure a desired edge. In particular, the setting of an image processing parameter for edge detection is complex. It is difficult to set a proper parameter without knowledge about image processing. Further, a problem arises in that since the optimum value is determined by repetition of setting and measurement, time is required.

It is also unclear to which portion (such as the width of a top portion or the bottom, or the width at other position) of an actual three-dimensional form pattern the pattern edge position decided on the SEM image for measurement corresponds. A problem arises in that it is difficult to accurately evaluate a three-dimensional form of an actually formed pattern.

SUMMARY OF THE INVENTION

It is therefore an object of the present invention to easily set an image processing parameter necessary to measure a desired point using an SEM with respect to a target pattern having such complex shapes. It is another object of the present invention to make it possible to accurately evaluate a three-dimensional form of an actually formed pattern without destruction.

In the present invention, an image processing condition for detecting a point designated by an operator on an SEM image is determined by calculating points characterized on the image and selecting the corresponding point.

In the present invention as well, points characterized on an SEM image are calculated and displayed. An operator selects the optimum one from within the displayed result and thereby sets the optimum measurement image processing condition.

Further, in the present invention, sectional shape model data of a pattern intended for evaluation and a simulation electron beam image of model data generated by electron beam simulation are used to set an image processing condition most suitable for measurement of a prescribed point.

According to the present invention, when a desired point of a target pattern having complex shapes is measured using an image detected by use of an SEM, it is feasible to easily set an image processing parameter necessary to measure the desired point.

According to the present invention as well, it is possible to accurately evaluate a sectional shape and/or three-dimensional form of an actually formed pattern without destruction and confirm the difference between the result of evaluation and a target value. As compared with the case in which information about the conventional sectional shape and/or three-dimensional form is not obtained, it is possible to improve the accuracy of management and control of a manufacturing process.

These and other objects, features and advantages of the invention will be apparent from the following more particular description of preferred embodiments of the invention, as illustrated in the accompanying drawings.

BRIEF DESCRIPTION OF THE DRAWINGS

FIG. 1 is a flow diagram for describing a pattern dimension measuring condition setting procedure according to a first embodiment;

FIGS. 3A through 3F are each a cross-sectional view showing a pattern structure intended for measurement;

FIG. 6A illustrates an SEM image;

FIG. 6B is a signal waveform diagram showing one scan line of the SEM image;

FIG. 6C is a diagram showing a signal waveform obtained by adding signal waveforms corresponding to respective scan lines in an N line addition region 6000 of FIG. 6A;

FIG. 6D is an SEM image/addition signal waveform diagram showing a state in which the added signal waveforms each shown in FIG. 6C are acquired over a plurality of regions of the SEM image;

FIG. 6E illustrates an SEM image of a circular pattern, one-scan-line waveforms of the SEM image and a signal waveform obtained by adding the one-scan-line waveforms;

FIG. 16A is a flow diagram showing condition-offering off-line work according to a sixth embodiment;

FIG. 16B is a processing flow diagram at the measurement of an actual pattern;

FIG. 23A is a cross-sectional view of a pattern obtained in the ninth embodiment and shows a reflected electron image as viewed from the left side of the pattern;

FIG. 23B is a cross-sectional view of a pattern and shows a reflected electron image as viewed from the right side of the pattern;

DESCRIPTION OF THE PREFERRED EMBODIMENTS

Preferred embodiments of the present invention will hereinafter be described with reference to the accompanying drawings.

First Embodiment

FIG. 1 shows the flow of processing of a pattern evaluating method according to a first embodiment of the present invention. In the pattern evaluating method according to the present embodiment, pattern-measuring condition offering using an SEM image can be easily realized through the use of image processing and a graphical user interface (hereinafter called "GUI"). FIG. 1 shows an image processing condition offering procedure.

To begin with, a wafer formed with normal patterns intended for evaluation is loaded (Step 1001) and wafer alignment is executed (Step 1002). Although the details thereof are omitted, information necessary for measurement, such as a chip arrangement on the wafer, etc. are inputted in advance, and a chip used for condition setting is designated (Step 1003).

Next, a length measuring position on the chip is designated using an optical microscope and an SEM image (Step 1004). At this time, an image at a measuring point, which is used for measurement alignment at the execution of automatic measurement, is stored as a template. A shift or movement of the wafer to a measuring position at the automatic length measurement may be performed such that a pattern coincident with the template is searched around the designated coordinates using the template. When the measuring point in the chip is determined, the wafer is moved in such a manner that an image at a measuring position designated by a stage can be acquired (Step 1005). Then, the magnification and rotation (in a beam scan direction) of an image used for measurement are set (Step 1006) and the image for measurement is picked up (Step 1007).

Figure 5A:
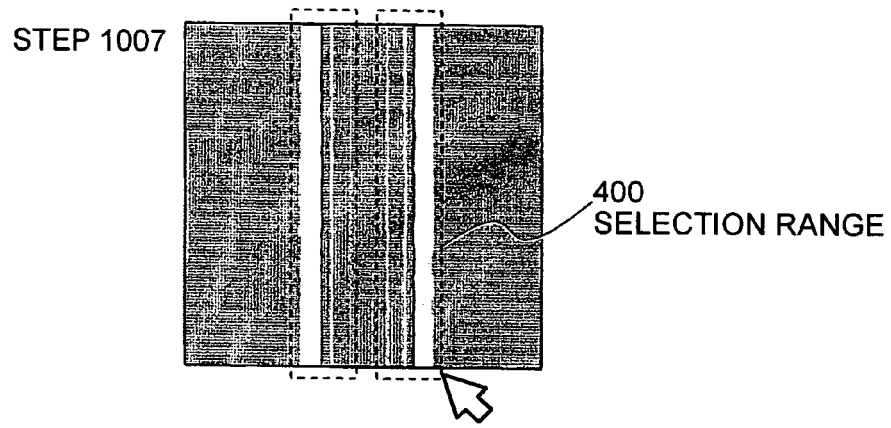
FIGS. 5A, 5B and 5C each show an SEM image of a pattern intended for measurement.

After the image of the pattern intended for measurement has been picked up in this way, the determination of a measuring point in the image and the setting of image processing parameters are carried out (Step 1020). The present embodiment provides a means for easily performing the determination of the measuring point and the setting of the image processing parameters (Step 1020). When the image is acquired, a processing region is first designated (Step 1008). As shown in FIG. 5A, an operator clicks on an edge point of a pattern that the operator desires to measure on the image through the use of a mouse or a pointing device to designate a selection range 400.

This processing is done to record how the edge of the pattern to be processed is placed on the pattern image and to place processing-nonrequired regions in parts in advance for the purpose of avoiding a failure at the automatic measurement. The present selection range is recorded together with the template for the measuring position search. Upon actual length measurement, the present measurement range may be applied to the corresponding pattern position after the positioning or alignment has been effected on the whole image. At this time, as shown in FIG. 5A, the selection ranges 400 are designated to the left and right edges of measured dimensions.

Figure 5B:
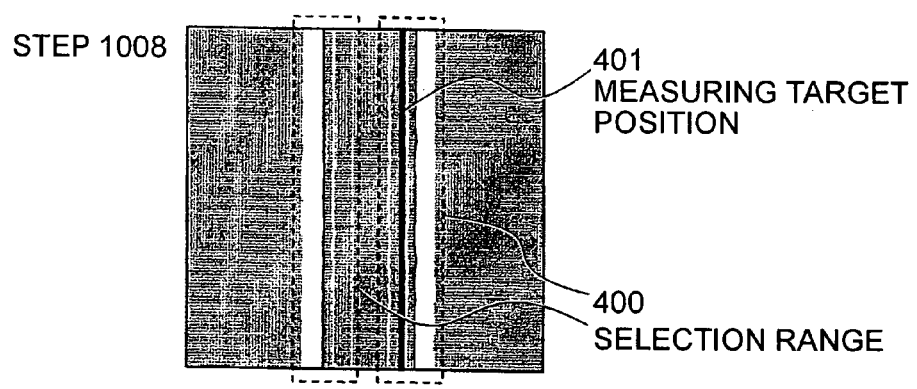

Next, each of pattern edges for actually measuring dimensions is designated within the region specified at Step 1007 (Step 1008). As shown in FIG. 5B, a measuring target position 401 (expressed in linear form in FIG. 5B) is designated by a cursor displayed on the screen by use of the mouse or the like. Although the shape of the target pattern might not be linear due to roughness of the edge or the like, a rough location may be designated. Each edge to be measured is determined by the operator in this way.

Next, an image processing condition for detecting the edge designated at Step 1009 is automatically calculated. The details of the image processing condition calculating process will be explained in detail with reference to FIGS. 6 through 8.

A line profile signal for an image to be processed is first generated. If noise is sufficiently low, then each line of an acquired image may be used as it is. Since an SEM image is generally low in S/N, a waveform 6002 set for each line is averaged over N lines (equivalent to a few tens of lines to a few hundreds of lines) within an addition region 6000 of an electron beam image 6001 as shown in FIGS. 6A through 6C to eliminate noise, thereby generating a line profile 6003, followed by execution of the processing.

As shown in FIG. 6D, the image can also be processed in plural parts along a pattern direction (upward and downward directions in FIG. 6C. This is effective for the case in which the dimensions of the pattern vary according to the locations due to line edge roughness or the like. As shown in FIG. 6E, a noise eliminating process can similarly be performed even on a circular pattern such as a hole pattern by acquiring a profile lying in the direction normal to a pattern edge intended for measurement. Firstly, an outer peripheral edge 6006 of a hole pattern on an electron beam image 6001 of FIG. 6E is first extracted. Next, the axes (x1, x2, . . . , xn) orthogonal to the outer peripheral edge 6006 are set. One line waveform 6002 on the set axes is determined. Now, these axes are set to the number lying in a range enough for noise elimination and sufficiently small in shape change.

A plurality of edge positions 6007 (each of which may coincide with the outer peripheral edge 6006) of one line waveform obtained in this way are aligned and averaged so that a line profile can be created in a manner similar to the line pattern. Since such processing becomes difficult when the pattern shape is complex, the number of integrations at the acquisition of the electron beam image may be increased (the SEM image is generally improved in S/N by applying an electron beam to the same point plural times and integrating the resultant signals) or smoothing processing may be performed before the creation of the profile.

Figure 7A:
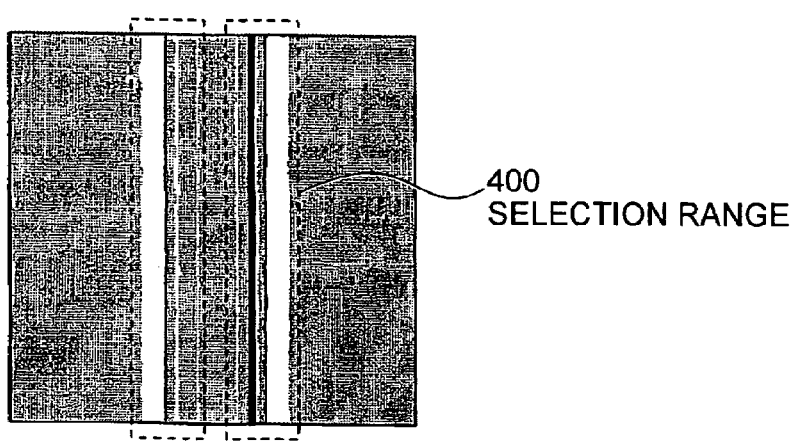
FIG. 7A illustrates an SEM image.
Figure 7B:
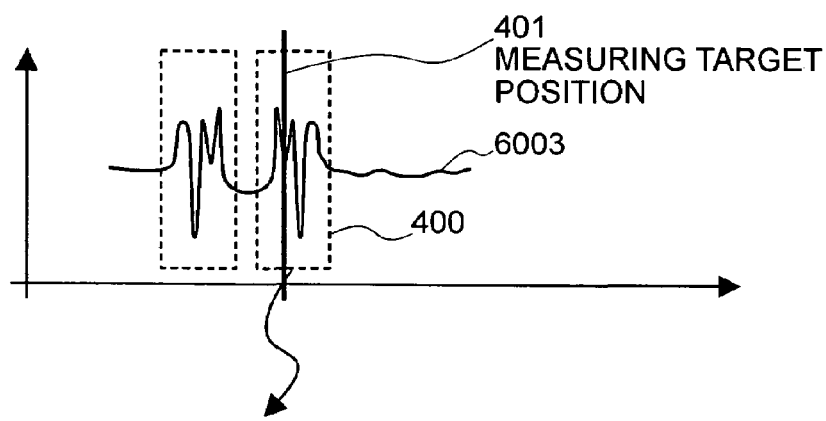
FIG. 7B is a signal waveform diagram showing a line profile of the SEM image.
Figure 7C:
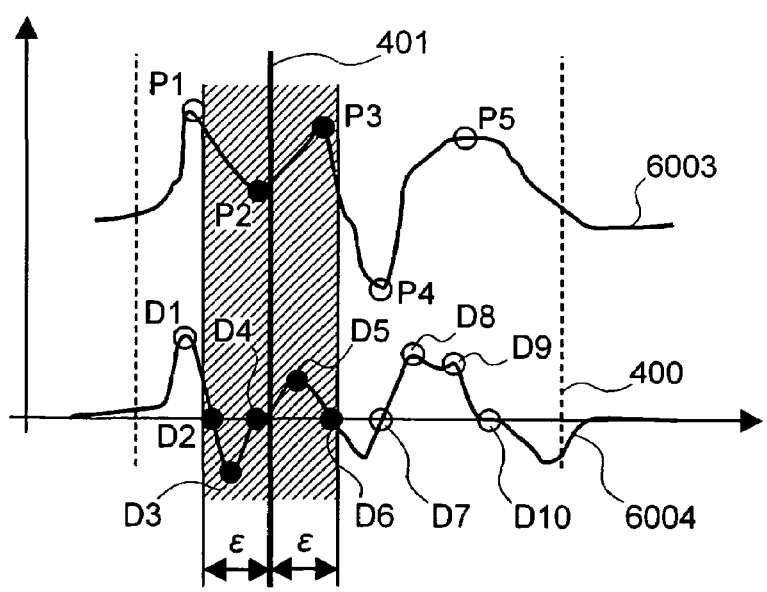
FIG. 7C is a waveform diagram illustrating a primary differential waveform corresponding to an enlarged waveform of a selected range 400 of the line profile of the SEM image.

Next, the final measuring position is determined within the section range 400 at the edge periphery designated by the operator. FIGS. 7A, 7B and 7C show an example of an SEM image signal waveform, wherein FIG. 7A depicts an image, FIG. 7B illustrates a waveform of a line profile, and FIG. 7C shows an enlarged view of FIG. 7B. Each of dotted lines indicates a selection range 400 lying on an edge periphery set by the operator, and the vertical straight line indicates the measuring target position 401 set at Step 1008. FIG. 7C shows an enlarged view of a detected line profile waveform 6003 and its primary differential waveform 6004.

First, the area for each distance $\epsilon$ from the measuring target position 401 is determined (this is represented using thin vertical solid lines). This distance $\epsilon$ is set to a suitable value in consideration of variations in setting, a variation in pattern edge position (edge roughness), etc. Next, points distinctive in terms of image signal lying within the area $\pm\epsilon$, such as points (P2 and P3) where local maximum and minimum values of the signal are taken, points (D2 through D6) which show a local maximum and a local minimum of a differential waveform or which intersect zero, points (not shown) set if necessary, which show a local maximum and a local minimum of secondary differentiation or which intersect zero, etc. are searched. These points are taken as candidates for measuring positions and the result of processing is displayed on the screen.

Figure 5C:
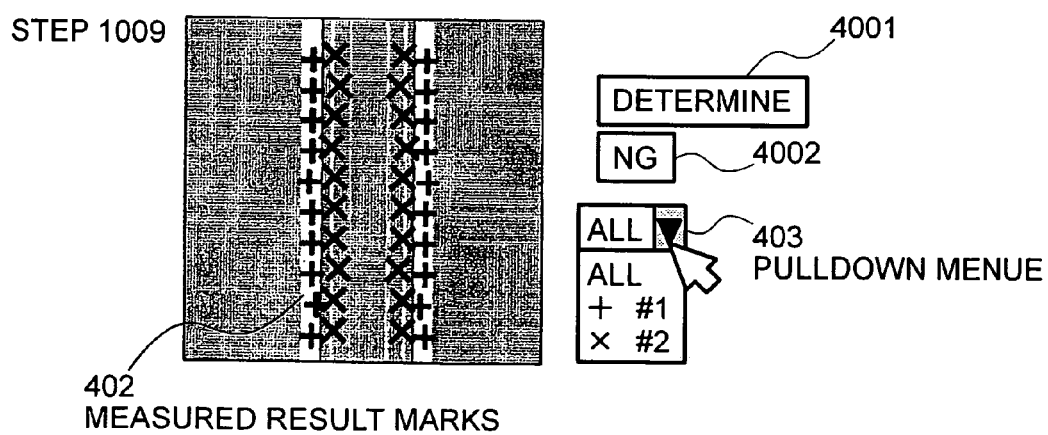

FIG. 5C shows one example of the result display. Although only two types are displayed for simplification in FIG. 5C, all the measured points are actually displayed, and the designated marks are selectively displayed through the use of a pull-down menu 403 or the like. The operator selects a measured result close to the designated measuring position and is able to easily confirm whether the result is good or not. While the points are being expressed in marks (x, +) as shown in FIG. 5C in the present example, it is further easy to understand the points if marks or the like different in color are used. If the points distinctive in image signal calculated in this way are displayed together with the image and the condition having the result closest to a desired measuring position is selected, then an image processing parameter for detecting a desired edge position can be easily determined.

The reason why the measured results are displayed in plural forms along the patterns as viewed in a y direction (vertical direction as viewed in FIG. 5C) in FIG. 5C, is that as shown in FIG. 6D, line profile waveforms 6003 are calculated with respect to plural regions (overlapped regions in the example of FIG. 6D: 1, 2, 3, . . . , M−2, M−1, M), and results obtained by subjecting them to the same processing are displayed. Such measurement is performed not only to evaluate the state of a change in line edge (line edge roughness) but also to confirm in conjunction with it, whether the proper result is obtained even with respect to a subtle difference in shape and a difference in noise by setting many regions in the y direction and scoring evaluation points. Such parameters that these all points are detected properly, can be judged to be stable.

In order to evaluate uniformity in the plane of the wafer, the points are normally measured with respect to a plurality of chips as in the case of five or nine points within one wafer. Consequentially, processing results relative to images of the plural chips are confirmed even at the condition setting. Thus, it is possible to evaluate whether the point measurement is made possible stably even when the pattern shape varies. For example, Steps 1005 to 1007 shown in FIG. 1 are previously repeated with respect to all measurement chips in the wafer and the images of the plural chips are stored. At Step 1011, processing is effected even on the previously picked-up plural images. Then, the results of such processing are displayed on the screen and whether the results are good or not, may be decided while looking at the whole result.

If the result of measurement obtained in this way is satisfactory, then the result of measurement is selected and an image processing condition is determined. As shown in FIG. 5C, a "Determine" button 4001 and an "NG" button 4002 are prepared. If a satisfactory result is obtained, then the result of measurement is selected and the "Determine" button is pushed. If a suitable one is not given, then the "NG" button 4002 is pushed to make it possible to set a further detailed condition.

Figure 2A:
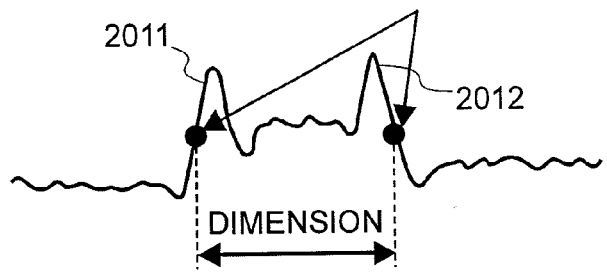
FIGS. 2A, 2B and 2C are each an SEM signal waveform diagram for describing a conventional pattern measuring method.
Figure 2B:
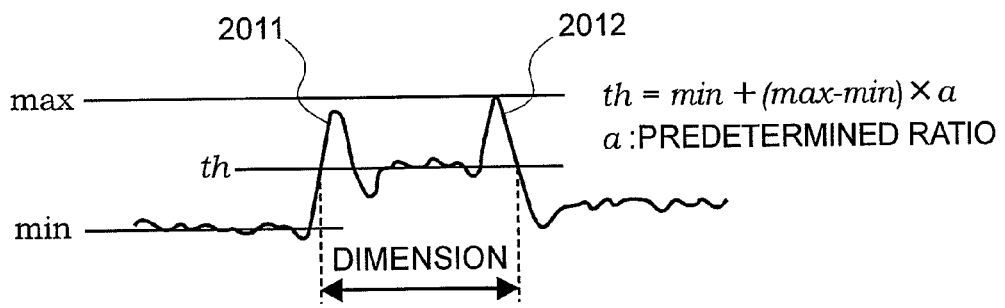
Figure 2C:
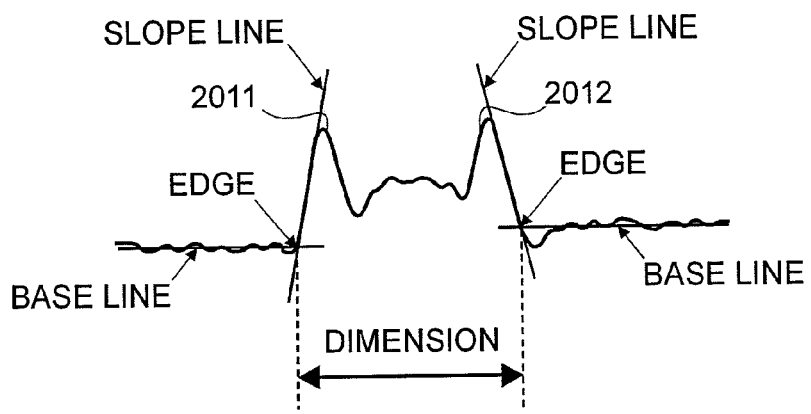
Figure 4A:
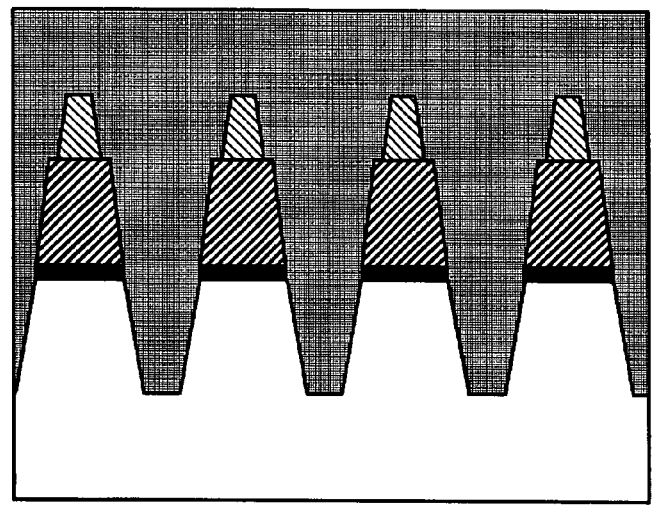
FIG. 4A is a cross-sectional view of a pattern intended for measurement.
Figure 4B:
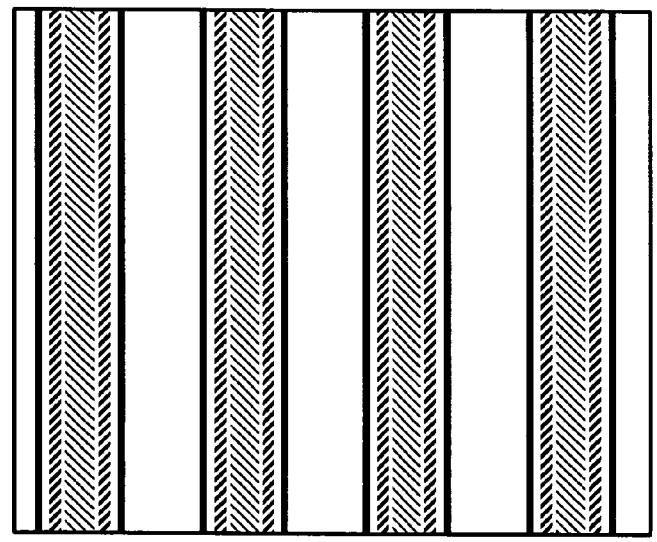
FIG. 4B is an SEM image of the pattern.
Figure 4C:
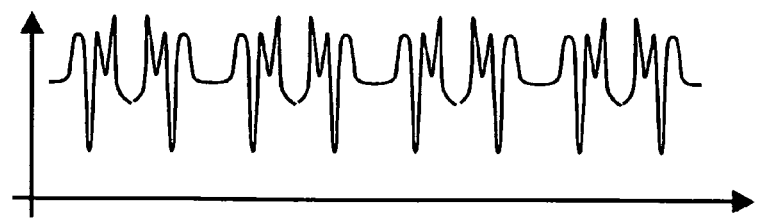
FIG. 4C is a signal waveform diagram of the SEM image shown in FIG. 4B.
Figure 8:
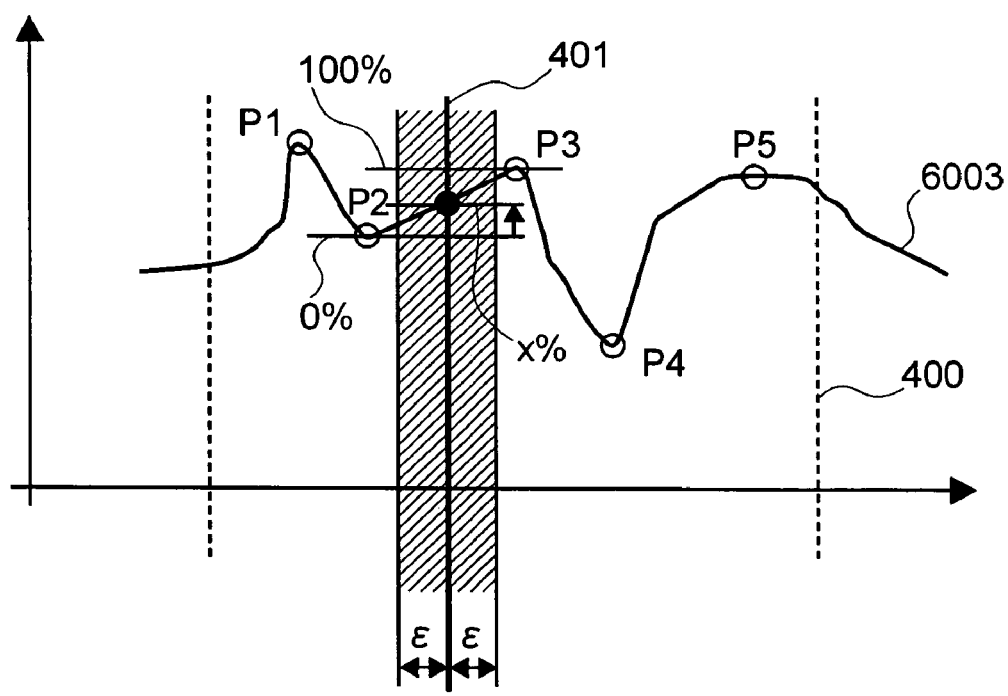
FIG. 8 is a waveform diagram depicting an enlarged waveform of a selected range 400 of a line profile of an SEM image.

When the suitable point is not extracted nearby at Step 1010, it is possible to set a suitable threshold value between the already-extracted pattern edges. An example thereof is shown in FIG. 8. This will be described using only an SEM signal amount waveform for simplification in FIG. 8. As shown in FIG. 8, points showing local maximum values (P2 and P3) and a local minimum value (P4) of the signal amount waveform are out of a proximal region of $\pm\epsilon$ as viewed from a measuring target position 401. When locations where no suitable results are obtained even at the detection of points distinctive in terms of other images, are designated, processing using such a threshold method as shown in FIG. 2B may be effected on some of the signal waveform.

In the case of the example shown in FIG. 8, the peaks (P2 and P3) on both sides of the measuring target position 401 are searched, and the point at a signal amount X % between P2 and P3 is detected assuming that a signal amount of P2 is 0 and a signal amount of P3 is 100, and the detected point is defined as an edge position candidate. Results obtained by suitably changing the value of X are displayed. The operator is caused to select the satisfactory result thereof in a manner similar to FIG. 5C.

Thus, the point distinctive in terms of an image signal and the points around the point with the point as the reference are displayed and selected as candidates, so that an image processing condition for detection of a desired edge position of the operator can easily be set. When the left and right patterns are symmetrical, an edge detecting process may be effected even on the opposite edges under the same condition. When they are different in structure, desired measuring positions are set to both edges in like manner, and image processing condition offering may be executed.

By imaging a specimen by an SEM using the image processing parameters set in this way and subjecting it to image processing, and measuring the distance between the edge positions, dimensional measurements made on the desired position can be realized.

Incidentally, although the measured results made under the plural conditions are displayed and the selection thereof by the operation is performed in the embodiment, the condition under which the closest result is given, may of course be set to the preset measuring target position 401 automatically. The setting of the measuring position is not necessarily limited to one point with respect to one image. Second and third measuring positions may be set as needed.

Figure 9:
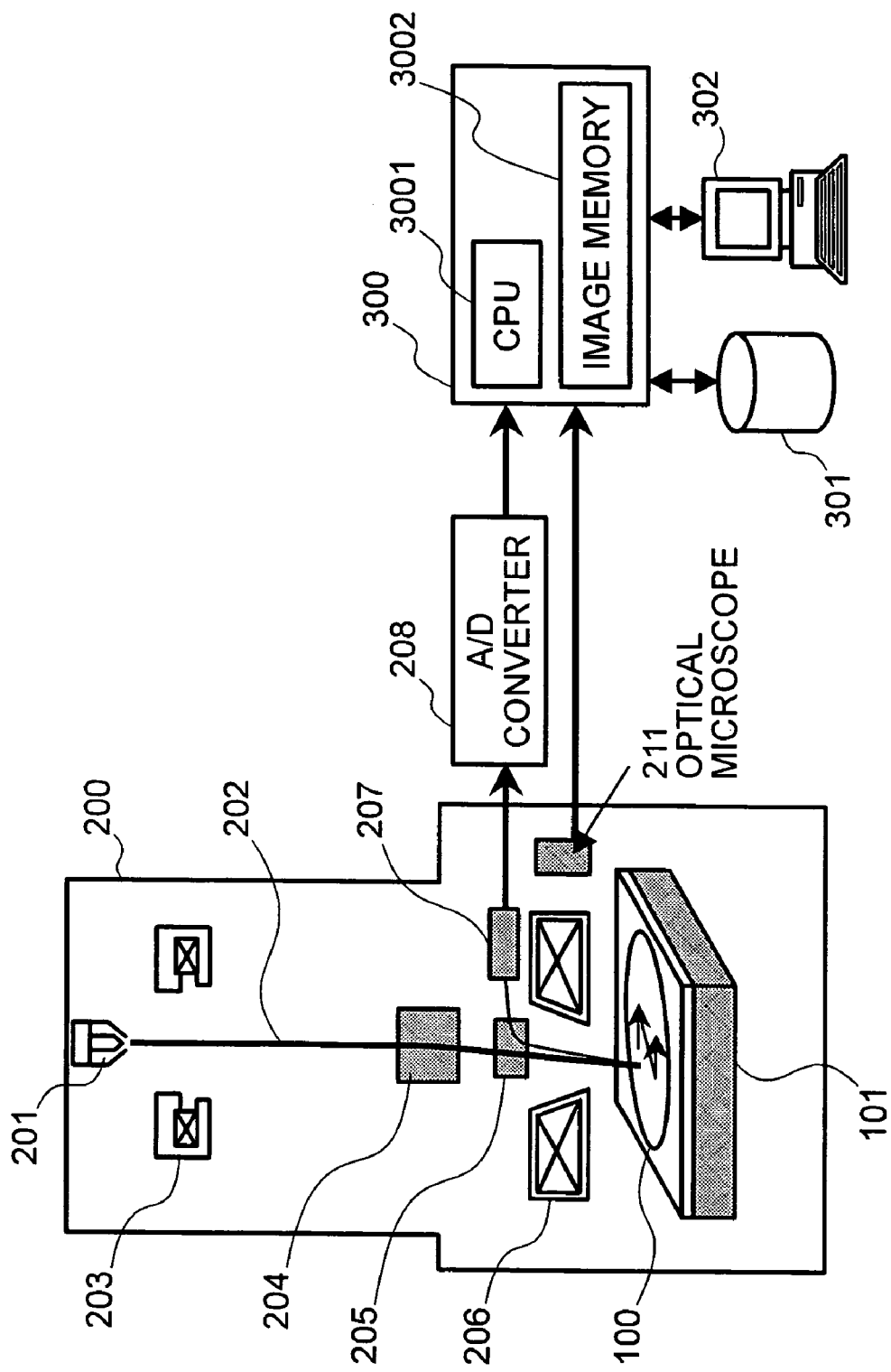
FIG. 9 is a front view showing a schematic configuration of an evaluation system according to the first embodiment.

FIG. 9 is a block diagram showing a configuration of an SEM 200 for pattern evaluation. In FIG. 9, a primary electron beam 202 emitted from an electron gun 201 is converged by condenser lenses 203 and focused onto and applied to a wafer 100 placed on a stage 101 through a beam deflector 204, an ExB deflector 205 and objective lenses 206. When the electron beam is applied thereto, a secondary electron is generated from the wafer 100. The secondary electron generated from the wafer 100 used as a sample or specimen is deflected by the ExB deflector 205 and detected by a secondary electron detector 207. A two-dimensional electron beam image is obtained by performing two-dimensional scanning of the electron beam by the deflector 204 or repetition scanning of the electron beam in an X direction by the deflector 204, and detecting the electrons generated from the sample in sync with the continuous shift or movement of the wafer in a Y direction by the stage 101.

The signal detected by the secondary electron detector 207 is converted into a digital signal by an A/D converter 208, which in turn is sent to an image processor 300. The image processor 300 includes an image memory 3002 for temporarily storing a digital image therein and a CPU 3001 which calculates a line profile and a characteristic amount from the image on the image memory 3002. Further, the image processor 300 also includes a storage medium 301 for storing the detected image or line profile, or the calculated pattern shape information or the like therein.

A display device 302 is connected to the image processor 300 and capable of realizing the operation of a necessary device, confirmation of the result of detection, etc. by means of a graphical user interface (hereinafter described as "GUI"). The length measuring SEM 200 includes an optical microscope 211 and drives the stage 101 if required to move or shift the sample wafer 100 from the observation field of view of the length measuring SEM 200 to the field of view of the optical microscope 211, thereby enabling even acquisition of an optical microscope image of the sample wafer 100.

The dimensions of patterns formed on the sample can be sequentially measured using the length measuring SEM 200 to which image processing parameters are set by the above-described procedure. The image processing parameters are set by the procedure shown in FIG. 1 and automatic length measurement of the wafer 100 is executed, whereby even an operator having no knowledge about image processing is capable of easily measuring the dimensions of a desired pattern portion.

Thus, according to the first embodiment, the condition for measuring a desired position can be easily set even to a pattern image complex in structure. Since the present technique is in no need of the knowledge about the image processing, the operator needs no skill. Although the image processing condition is set to the sample complex in shape in the embodiment, the present method can be applied even to the sample of the conventional simple structure. Owing to the application of the present method, the setting of the condition becomes easy and the time required to set the image processing condition is shortened.

Second Embodiment

A second embodiment will be explained using FIG. 10. While the first embodiment has disclosed the means for determining the image processing condition under which the result close to the edge position designated by the operator is obtained, the second embodiment will explain a means for detecting points characterized in image signal in advance and allowing an operator to select a satisfactory result from the detected results.

Figure 10:
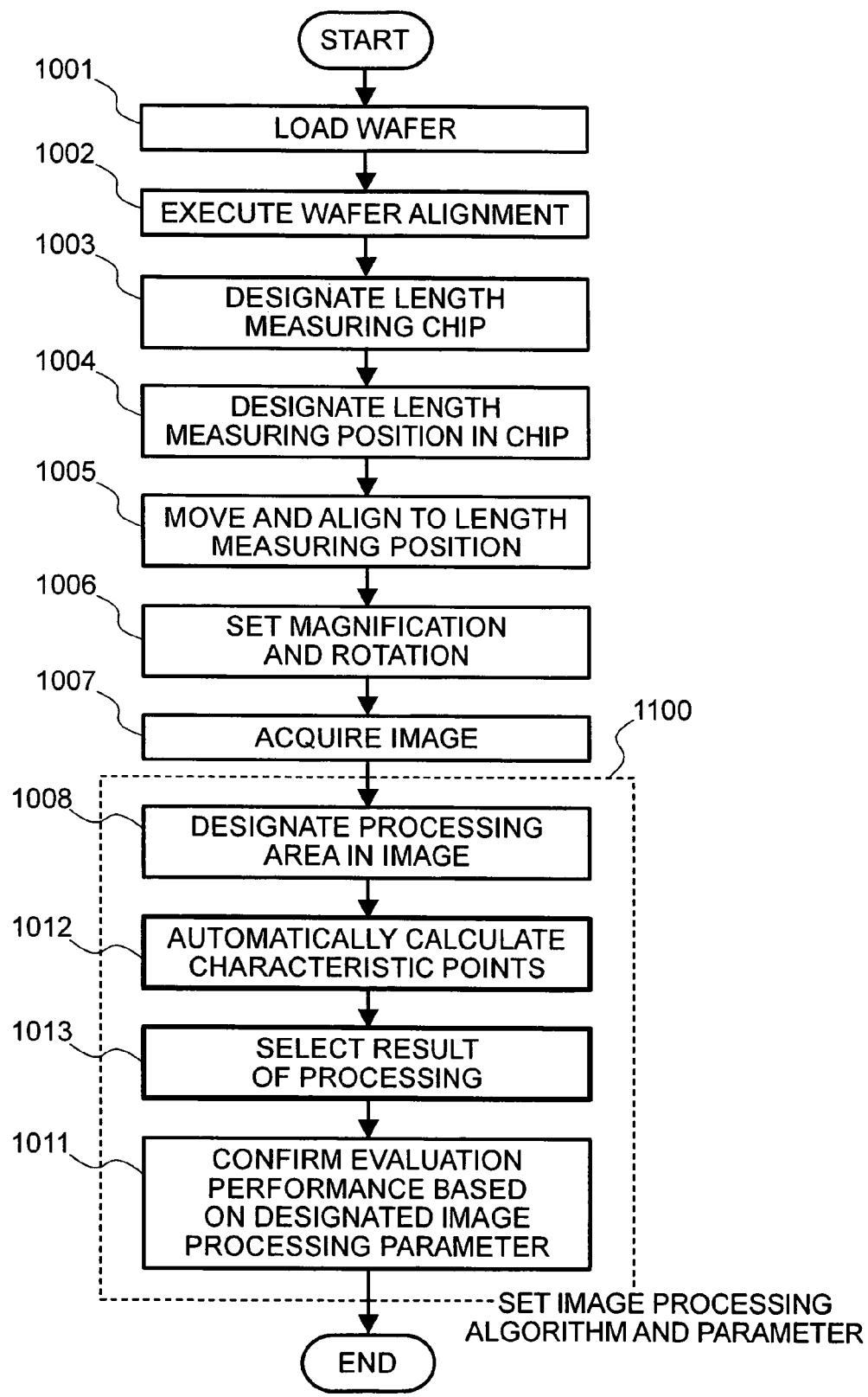
FIG. 10 is a flow diagram illustrating a pattern dimension measuring condition setting procedure according to a second embodiment.

The whole flow of the second embodiment is shown in FIG. 10. The second embodiment is different from the first embodiment in terms of Steps 1012 and 1013 showing determination of measuring points in an image and setting of image processing parameters (1100). Even in the case of the second embodiment in a manner similar to the first embodiment, an image intended for dimensional measurement is picked up (to Step 1007), and an edge existing area is set (Step 1008). Next, points characterized in image are calculated within the area designated at Step 1008 in a manner similar to FIG. 7C of the first embodiment without performing operator's designation (Step 1012). However, the calculation of the characterized points is performed over the whole selection range 400 for each edge existing position without being directed to ±ε as shown in FIG. 7C. The calculated results are displayed on the image in superimposed form in a manner similar to FIG. 5C.

Next, the operator selects the suitable calculated result from the calculated edge positions in a manner similar to FIG. 5C and confirms the result of measurement (Step 1011). The confirmation of the result of measurement is effected even on images of other chips as needed. Thus, the image processing condition used to obtain the selected result is defined as a processing condition at automatic measurement. Incidentally, the setting of the measuring position is not necessarily limited to one point with respect to one image. Second and third measuring positions may be set as needed.

Thus, according to the second embodiment in a manner similar to the first embodiment, the condition for measuring a desired position can be easily set even to a pattern image complex in structure. Since the present technique is in no need of the knowledge of the image processing, the operator needs no skill. Although the image processing condition is set to the sample complex in shape in the embodiment, the present method can be applied even to the sample of the conventional simple structure. Owing to the application of the present method, the setting of the condition becomes easy and the time required to set the image processing condition is shortened.

Third Embodiment

While the image processing condition at measurement has been determined using only the SEM image of the sample in each of the first and second embodiments, a third embodiment will explain a method for setting a more reliable image processing condition by using a geometric or form model of a target sample.

Figure 11:
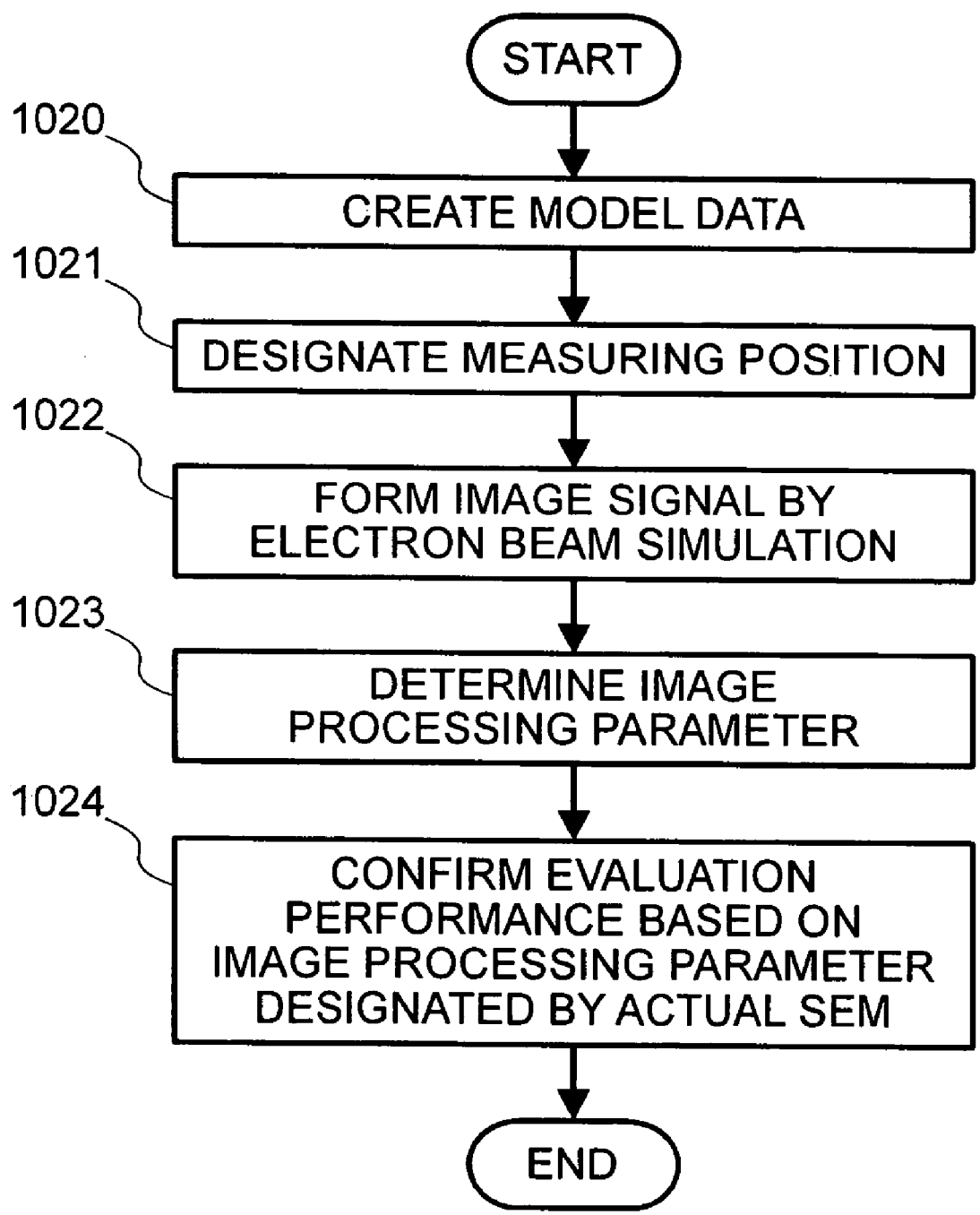
FIG. 11 is a flow diagram depicting a pattern dimension measuring condition setting procedure according to a third embodiment.

FIG. 11 shows a processing flow according to the third embodiment. In the third embodiment, model data 410 about the shape and material of a pattern intended for measurement is first created (Step 1020).

Figure 12A:
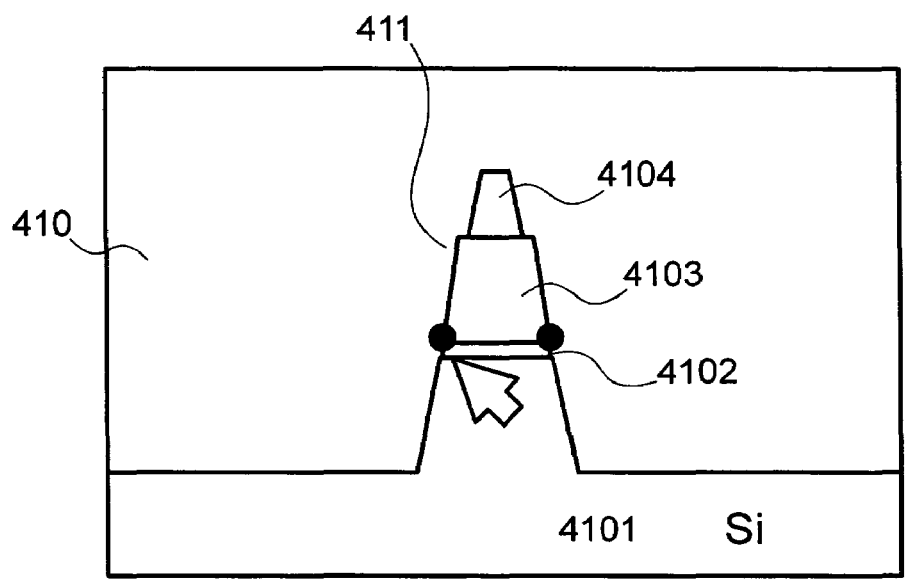
FIG. 12A is a pattern cross-sectional view showing a dimension measuring position of a pattern.

FIG. 12A illustrates one example of the model data 410. The present embodiment shows a case in which a silicon oxide film layer 4102, a silicon nitride ($Si_3N_4$) layer 4103 and a silicon oxide layer 4104 are stacked over an Si substrate 4101, and concave patterns are processed into the Si substrate by etching, whereby a layer structure pattern 412 is formed. As the model data, data about the dimensions (height, top and bottom widths) and materials of the respective patterns of the layer structure, and their positional relationships are recorded. The data may also be created by a system like graphics drawing tool or by such a method that the respective vertices are designated by coordinates. The data about the materials are added to their closed curves. A measuring point 411 is designated on the model data having such a sectional shape (Step 1021).

Next, a simulation electron beam signal 6005 of a target sample is generated by simulation or the like with the model data as the base (Step 1022). The simulation electron beam signal 6005 may be generated by any method if such a method that an image similar to an actual image can be formed, is adopted, as in the case of a method using the relationship among materials, tilt angles and signal amounts, etc. in addition to simulation using the Monte Carlo method or the like.

Figure 12B:
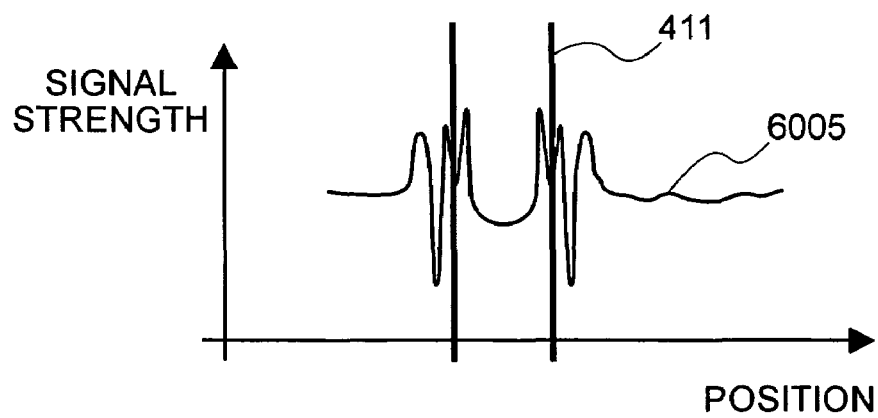
FIG. 12B is a signal waveform diagram illustrating a line profile of an SEM image of the pattern shown in FIG. 12A.

Next, the resultant simulation electron beam waveform 6005 is processed while an image processing parameter is being changed. Then, a characteristic point is searched from an image signal around the target measuring position 411 in a manner similar to the first embodiment. An image processing parameter at which such a searched characteristic point most often appears, is determined by selection based on such GUI as shown in FIG. 5C or automatic selection. Such an image processing parameter as to be used to calculate such result of measurement (vertical line 412 in FIG. 12B) that the characteristic point selected in this way most often appears, is defined as an image processing parameter used for actual measurement (Step 1023).

The processing so far can be executed by only the model data. Further, Step 1024 for confirming the correspondence to the actual image is executed as needed. At Step 1024, an image of an actual wafer is acquired in a manner similar to the first and second embodiments. Measurement based on the image processing parameter determined at Step 1023 is executed. As a result, if the result of measurement similar to the result relative to the simulation electron beam signal obtained by simulation is obtained, it is then judged that no problem arises. Thus, an image processing condition at this time is set as a measuring condition.

Thus, the third embodiment can easily set the condition for measuring a desired position even to a pattern image complex in structure in a manner similar to the first and second embodiments. Since the present method is in no need of the knowledge about the image processing, an operator needs no skill. The measurement of a point that the operator desires to measure truly can be easily realized using the model data. Therefore, the use of the present method makes it possible to reliably measure a point important in terms of process management and device performance. Incidentally, although the image processing condition is set to the sample complex in shape in the embodiment, the present method can be applied even to the sample of the conventional simple structure. Owing to the application of the present method, the setting of the condition becomes easy and the time required to set the image processing condition is shortened.

Fourth Embodiment

Figure 13:
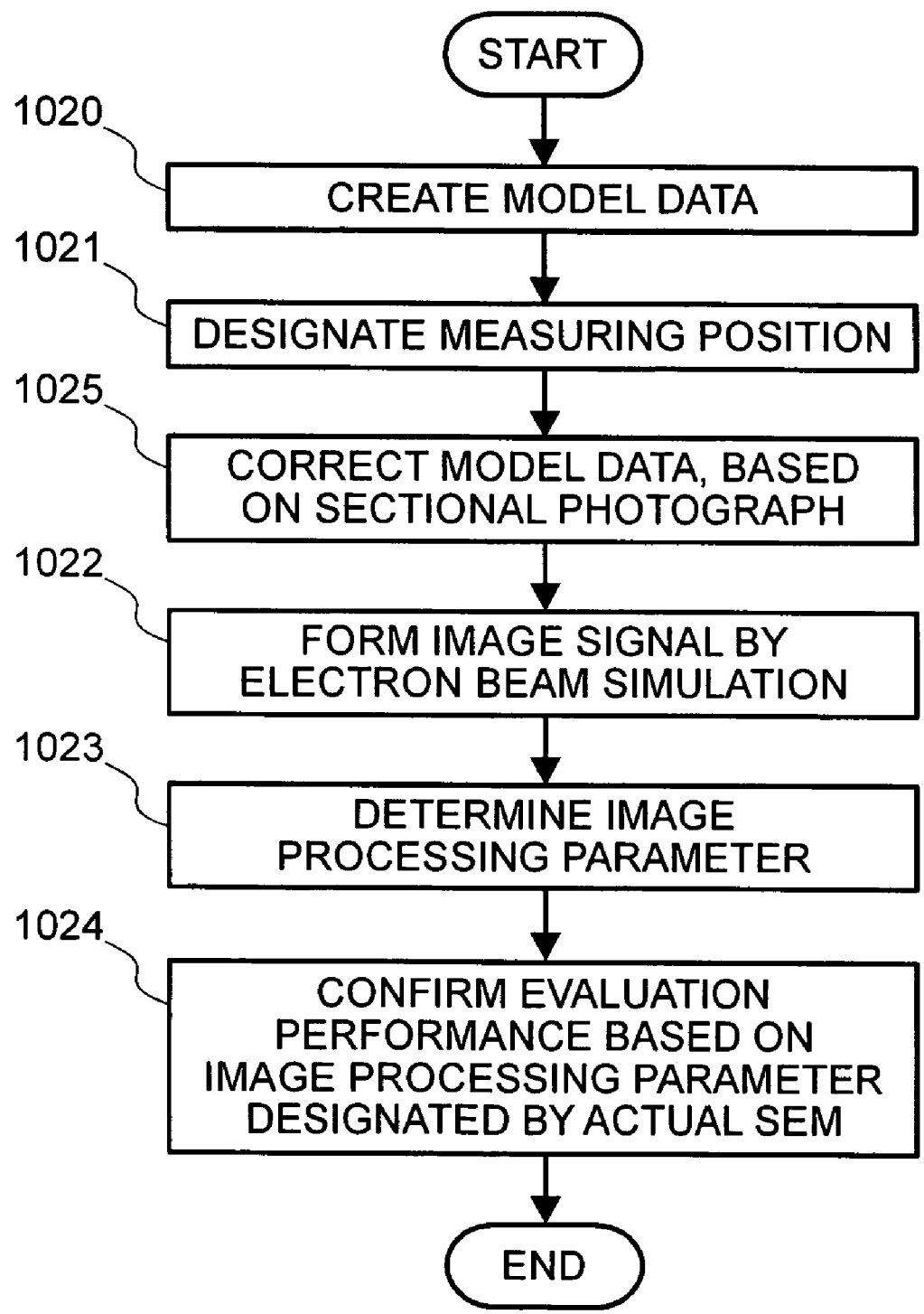
FIG. 13 is a flow diagram depicting a pattern dimension measuring condition setting procedure according to a fourth embodiment.

A fourth embodiment provides a means which adjusts the sectional structure model data used in the third embodiment using an actual sectional photograph and provides a result closer to an actual state. FIG. 13 is a diagram showing the flow of the fourth embodiment. A model data correcting step 1025 using a sectional photograph combined with a sectional image is added to the third embodiment after the measuring position designating step 1021.

Figure 14:
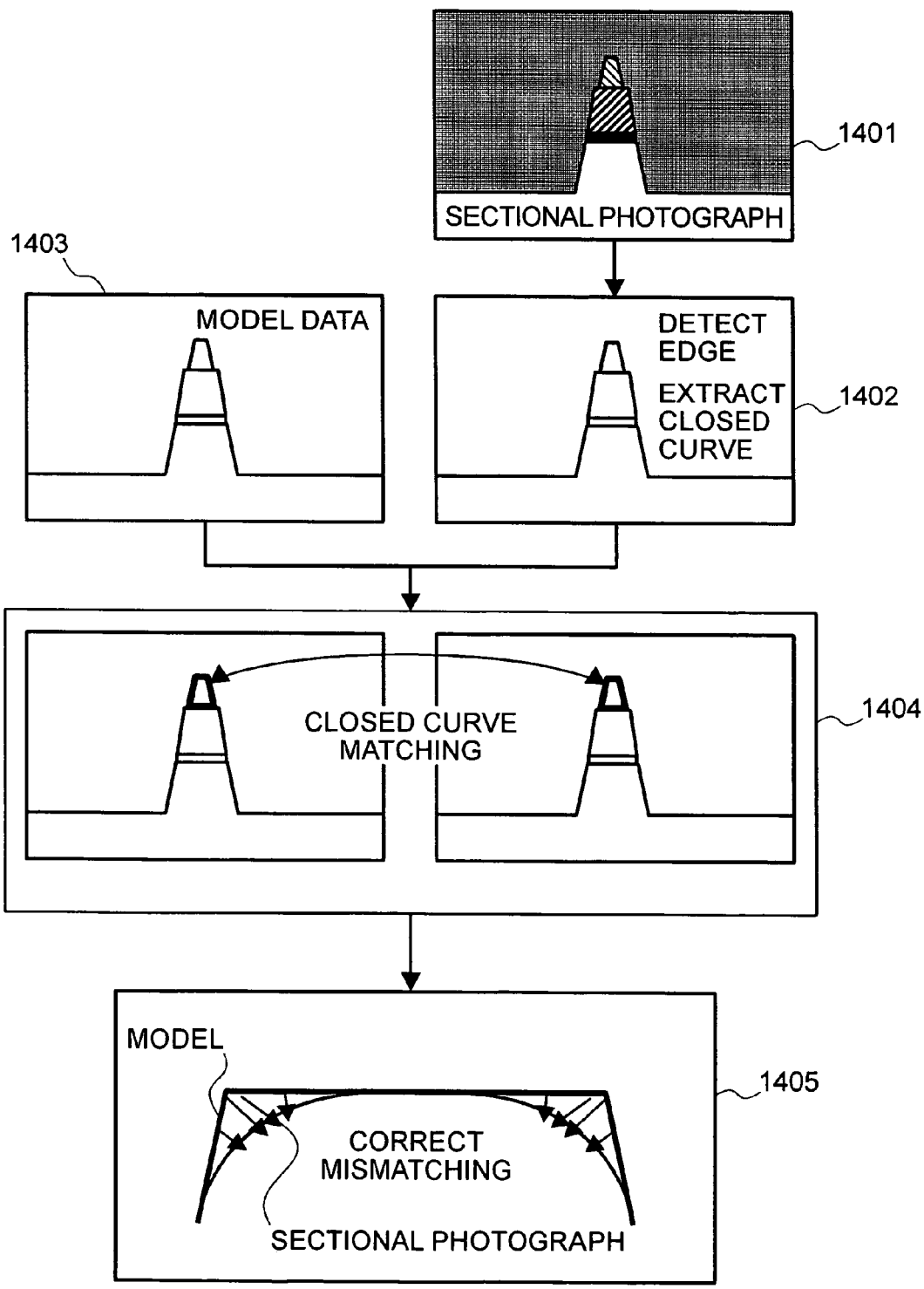
FIG. 14 is a flow diagram showing a processing procedure according to the fourth embodiment.

The state of processing is shown in FIG. 14. In a sectional photograph 1401, a pattern outer periphery is extracted by an edge detecting process 1402 and closed curves are formed for every element. These closed curves are matched with a closed curve existing in model data 1403 to cause the model data 1403 and the sectional photograph 1401 to correspond to each other (1404). In the sectional photograph 1401 and model data 1403 associated with each other in this way, each mismatched portion is detected to correct the model data (1405). In the model data in particular, each of corner portions 1406 results in an ideal curvature radius infinitesimal angle but is often rounded actually. Since an SEM signal is easy to change at the corner portions due to the edge effect or the like, the proper result of simulation cannot be obtained if their shapes are not brought into model form accurately. Therefore, the model data is corrected with these inconsistencies as the base. With the execution of the correction of the model data, a simulation electron beam signal is generated in a manner similar to the third embodiment and an image processing parameter for measuring a desired location is determined.

Thus, the fourth embodiment can easily set the condition for measuring a desired position even to a pattern image complex in structure in a manner similar to the first and second embodiments. Since the present method is in no need of the knowledge of the image processing, an operator needs no skill. The measurement of a point that the operator desires to measure truly can be easily realized using the model data in a manner similar to the third embodiment. Therefore, the use of the present method makes it possible to reliably measure a point important in terms of process management and device performance. A stabler and high-reliable condition setting is made possible by correcting the model data through the use of the sectional photograph. Incidentally, although the image processing condition is set to the sample complex in shape in the embodiment, the present method is applicable even to the sample of the conventional simple structure. Owing to the application of the present method, the setting of the condition becomes easy and the time required to set the image processing condition is shortened.

Fifth Embodiment

Figure 15:
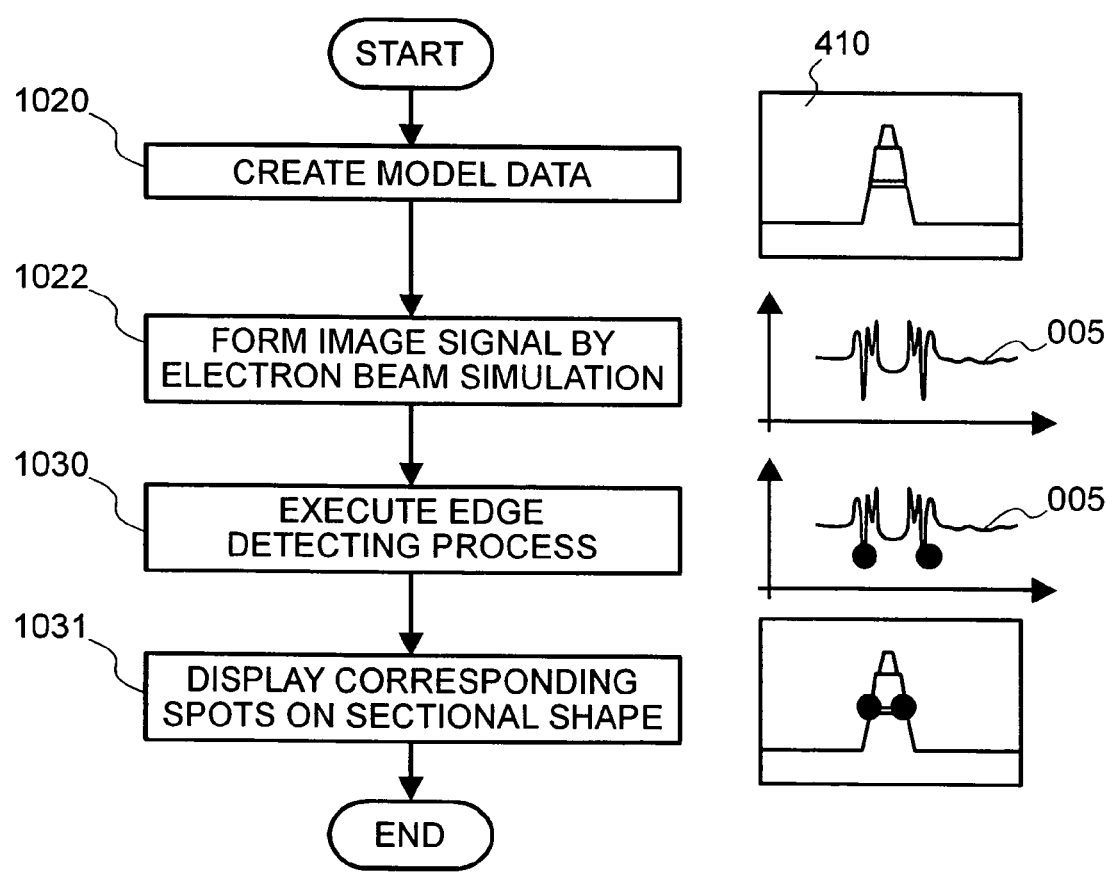
FIG. 15 is a flow diagram illustrating a measured point confirming method according to a fifth embodiment.

Since only the Top down View image of the SEM is used in the first and second embodiments, it is not clear to which portion of the actual sectional shape the measuring point desired by the operation corresponds. A fifth embodiment shows a means which realizes the function of displaying which portion of section is being measured under the image processing condition set in each of the first and second embodiments, using the form model data and simulation electron beam signal employed in the third or fourth embodiment. A flow of the fifth embodiment is shown in FIG. 15. Model data is first created in a manner similar to the third and fourth embodiments (Step 1020). Next, electron beam simulation is executed based on the created model data and thereby a simulation electron signal waveform is generated (Step 1022).

Incidentally, as the model data at this time, data corrected by the sectional photograph may of course be used in a manner similar to the fourth embodiment. Next, an edge detecting process is effected on the simulation electron beam waveform obtained at Step 1022, under the image processing condition set by the means of the first or second embodiment or other means (Step 1030). If a point corresponding to an edge position obtained on the sectional model data is finally displayed (Step 1031), then the corresponding measuring position based on the set image processing condition can be easily confirmed.

According to the fifth embodiment as described above, it is possible to easily confirm to which point the point measured by the SEM corresponds structurally. Thus, the present embodiment has the advantage that when the measuring point can be determined, it enables suitable adaptation to an abnormal process. Incidentally, although the image processing condition has been set to the sample complex in shape in the present embodiment, the present method is applicable even to the sample of the conventional simple structure.

Sixth Embodiment

A sixth embodiment will explain a means which estimates a sectional shape of a pattern on the basis of the result of dimensional measurement. A flow thereof is shown in FIGS. 16A and 16B. FIG. 16A shows condition-offering off-line work, and FIG. 16B is a flow at the time of actually performing dimensional measurement. First, the creation of model data (Step 1020), the generation of a simulation electron signal waveform (Step 1022) and edge detection under a designated image processing condition (Step 1030) are executed in a manner similar to the fifth embodiment. At this time, the edge detection is executed at plural points according to the structure. The correlation between each point measured at Step 1030 and the sectional model data is recorded at the end of off-line.

Next, wafer alignment, image acquisition alignment, etc. are executed upon actual process wafer measurement and thereafter an image of a pattern intended for measurement is acquired (Step 1050). Next, an edge detecting process is effected on the electron beam image obtained at Step 1050 under a pre-designated condition (the same as Step 1030) (Step 1051).

Next, the dimensions of the sectional model data are changed using the dimensions of the resultant respective points to create data for display (Step 1052). If a measured value of a bottom width of an undermost layer is thinner than the model data by 10 nm, for example, then 10 nm-thinned data is created. Finally, the created data is displayed on the screen as a sectional shape (Step 1053). There is a need to evaluate the height of a three-dimensional form too as well as the transverse dimension of the three-dimensional form. Since, however, the height of each pattern depends on a deposited film in many structures and the film thickness thereof is often managed with sufficient accuracy by another method such as a film-thickness meter, an approximate three-dimensional form can be estimated even at the evaluation of only the transverse dimension. Thus, the three-dimensional form can be estimated using the measured result and the model data. At this time, the height (thickness) of each layer is set using the result of film-thickness measurement or the specified value of the deposited film. These data are available from the film-thickness meter or design data via a network.

It is also possible to obtain a sectional shape by additionally measuring the height of each pattern and using its actually-measured data. In this case, examples of means for measuring the height of each pattern include scanning probe microscopes (SPM) such as a scanning tunneling microscope (STM), an atomic force microscope (AMF), and a near field optical microscope (NFOM), and an optical height detecting means which determines height from interference generated from the difference in optical path between lights reflected from a pattern and a steplike section. Results of measurements by these three-dimensional form measuring devices are available via a network in a manner similar to the film-thickness information.

Figure 17A:
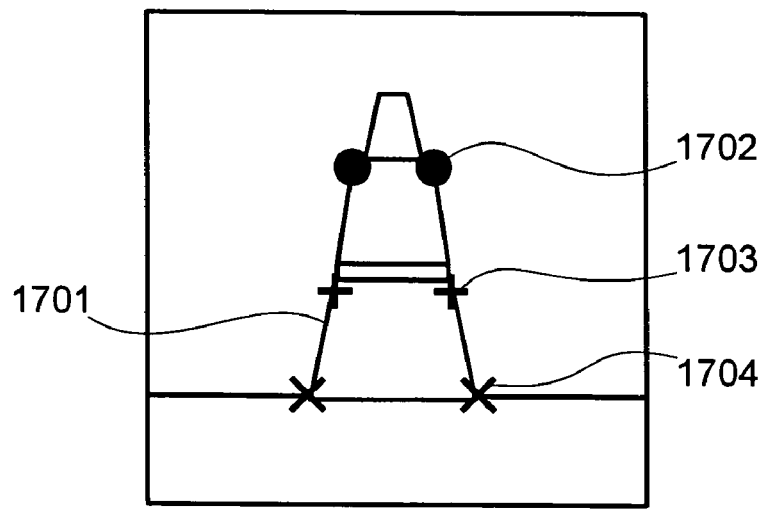
FIG. 17A is a cross-sectional view of a pattern, showing pattern dimension measuring positions according to the sixth embodiment.
Figure 17B:
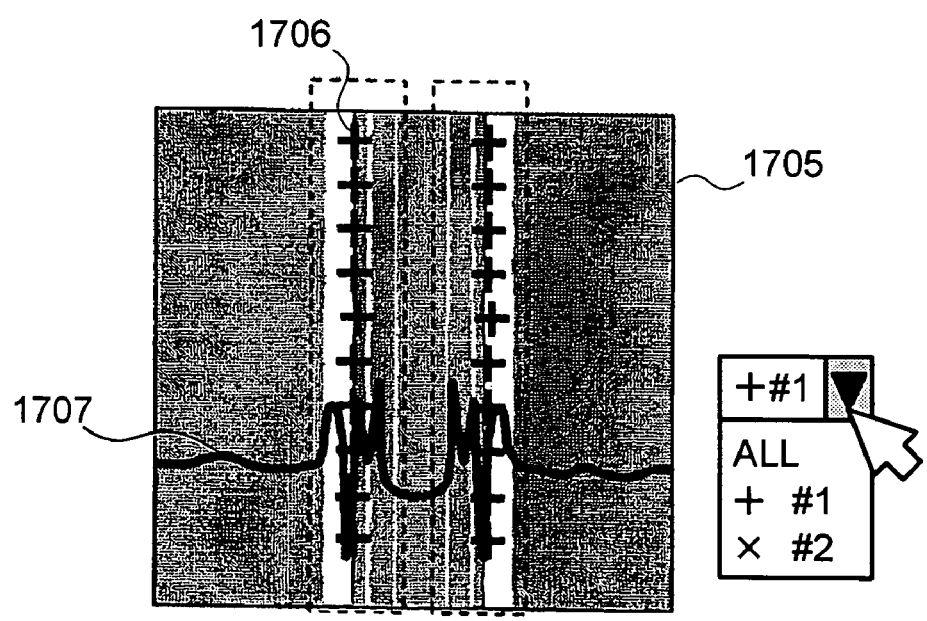
FIG. 17B is an SEM image illustrating the pattern dimension measuring positions and a signal waveform thereat.

FIGS. 17A and 17B show one example of a method for displaying the result of measurement. FIG. 17A is a sectional estimation result, and FIG. 17B is actual image data. The state of patterns can be easily confirmed by displaying these together. Since it is possible to designate a plurality of measuring points, measuring points 1702 through 1704 are represented on a sectional form 1701 by different patterns as shown in FIG. 17A, and where their corresponding points correspond on an image 1705 are displayed as designated at 1706 with being superimposed on the image of FIG. 17B. At this time, it is convenient if waveform data 1707 of an image signal is also displayed thereon in superimposed form.

Figures 27A, 27B:
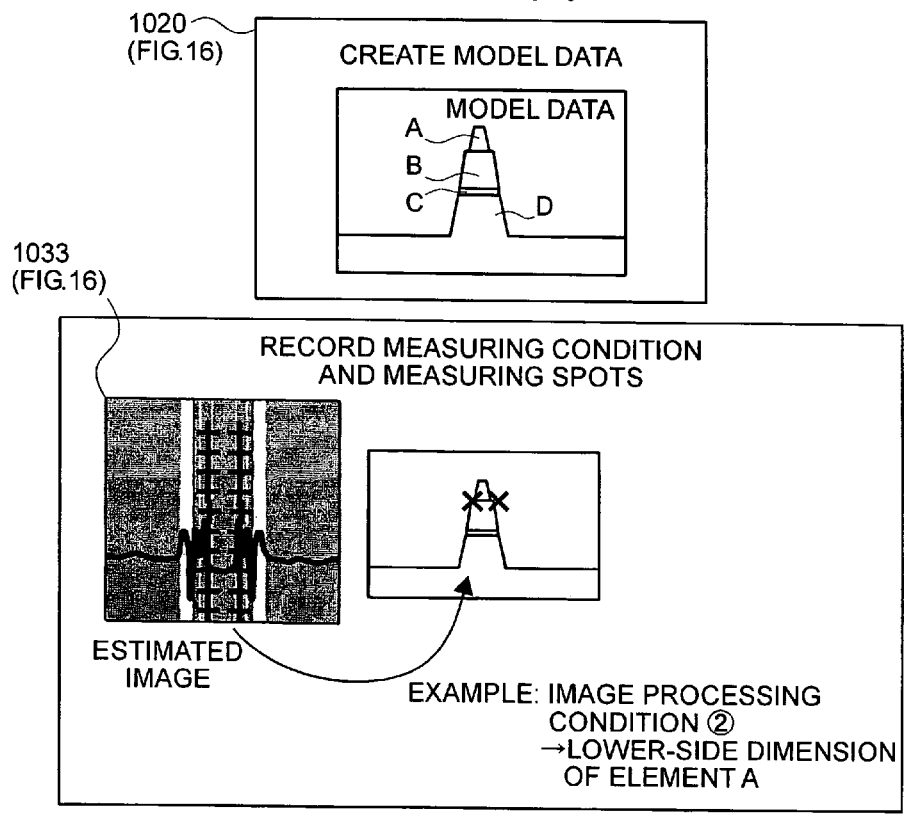
FIG. 27 is a diagram for describing a method for displaying the result of measurement of pattern dimensions obtained in the sixth embodiment.

FIGS. 27A and 27B show one example of data at the execution of the flow shown in FIGS. 16A and 16B. As shown in FIG. 27A, a measuring object can be divided for every element upon model data creation (Step 1020). Images based on electron beam simulation are formed, and where the results of measurement correspond on sectional images for every image processing condition, are recorded correspondingly as shown in FIG. 27B. Data at portions indicated by thick frames in FIG. 27B are values obtained by the actual process wafer measurement (FIG. 16B). By obtaining these data, a sectional three-dimensional form can be estimated where actual dimensions are reflected on the corresponding points of the model data.

In the sixth embodiment as described above, the sectional shape of each pattern intended for evaluation and the three-dimensional form based on it can be easily estimated by combining together the model data of the structure and the measured values obtained by the SEM. Thus, the present embodiment has the advantage that when the sectional shape and/or three-dimensional form can be estimated, suitable adaptation to an abnormal process is enabled. Incidentally, although the image processing condition has been set to the sample complex in shape in the present embodiment, the present method is applicable even to the sample of the conventional simple structure.

Seventh Embodiment

Figure 18:
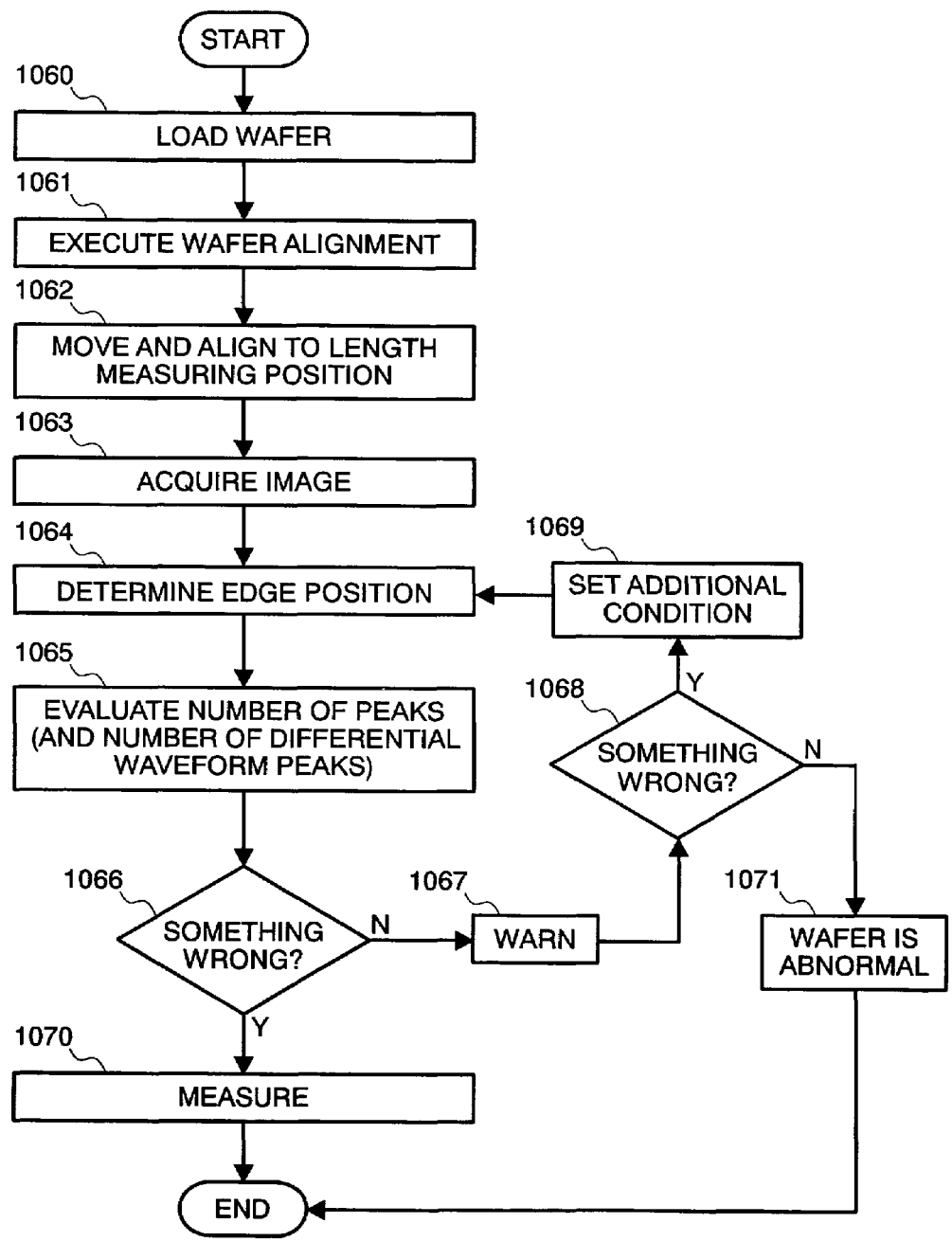
FIG. 18 is a flow diagram showing a pattern dimension measuring procedure according to a seventh embodiment.

A seventh embodiment will explain an example at the evaluation of a process wafer different from one used for setting, on the image processing conditions set by the methods described in the first through fourth embodiments or other method. FIG. 18 shows a flow of the seventh embodiment. A wafer intended for evaluation is first loaded into a measuring SEM (Step 1060). After execution of wafer alignment (Step 1061), a shift of the wafer to a length measuring position and its alignment are performed (Step 1062), followed by acquisition of an image of a pattern intended for evaluation (Step 1063). Next, the position of the edge existing area or range 400 set by each of the first through fourth embodiments is determined with respect to the resultant image by a technique such as template matching (Step 1064).

Next, the number of peaks of a waveform in the edge area 400 is evaluated to determine a measuring edge position (Step 1065). If the number of the peaks is identical to one at condition offering, then edge detection and measurement are performed on a predetermined condition with no abnormality (Steps 1066 and 1070). If similar evaluation is performed not only on the waveform peaks but also on the peaks of a differential waveform, then a higher reliable result is obtained. When the number of the peaks is different from one at the condition offering here, it is judged that something is wrong with the corresponding pattern, and warning is issued to an operator (Steps 1066 and 1067). In response to the warning, the operator looks at an SEM image of a target pattern and determines the presence or absence of a problem (Step 1068). When it is judged by the operator that the problem has arisen (something is wrong), the present wafer is eliminated from the measuring object as a defective wafer (Step 1071).

How the pattern is viewed changes depending on the workmanship thereof. There may be cases on occasion in which since how an image is viewed varies even if its variation within an allowable range occurs, it cannot be measured well. That is, they are a case where an edge to be seen is unsighted and a case where edges more than the estimated number are being in view. In the present embodiment, a check based on the number of waveform peaks is made to cope with or adapt to such a variation within the allowable range. When it is judged by confirmation of the SEM image that no problem occurs, an allowable value is set to a change in the number of peaks, and the condition is re-set so that no warning may be issued at its subsequent evaluation (Step 1069). This condition setting can be realized by allowing the operator to indicate the corresponding peaks through an image at condition offering and an image of the present pattern intended for evaluation and teaching the increased or decreased peaks.

According to the seventh embodiment, an error in measurement due to mismeasurement and an abnormal output can be avoided by determining whether the result of measurement is good or not. Thus, a higher reliable measurement result can be obtained. Updating the allowable range on the basis of operator's confirmation makes it possible to reduce the frequency of mismeasurement. Although the abnormality judgment has been made using the number of peaks in the embodiment, it is also feasible to make a judgment by holding an image in the normal case and using a difference from the image. For example, a normalized correlation between a sample image intended for measurement and the image in the normal case is made, and whether the measurement is normal or not, may be judged using correlation heights.

Eighth Embodiment

While the first through seventh embodiments have described the method for estimating the sectional shape and/or three-dimensional shape through the use of only Top-down view of the secondary electron image, an eighth embodiment will describe measurement performed using a tilt image.

Figure 19:
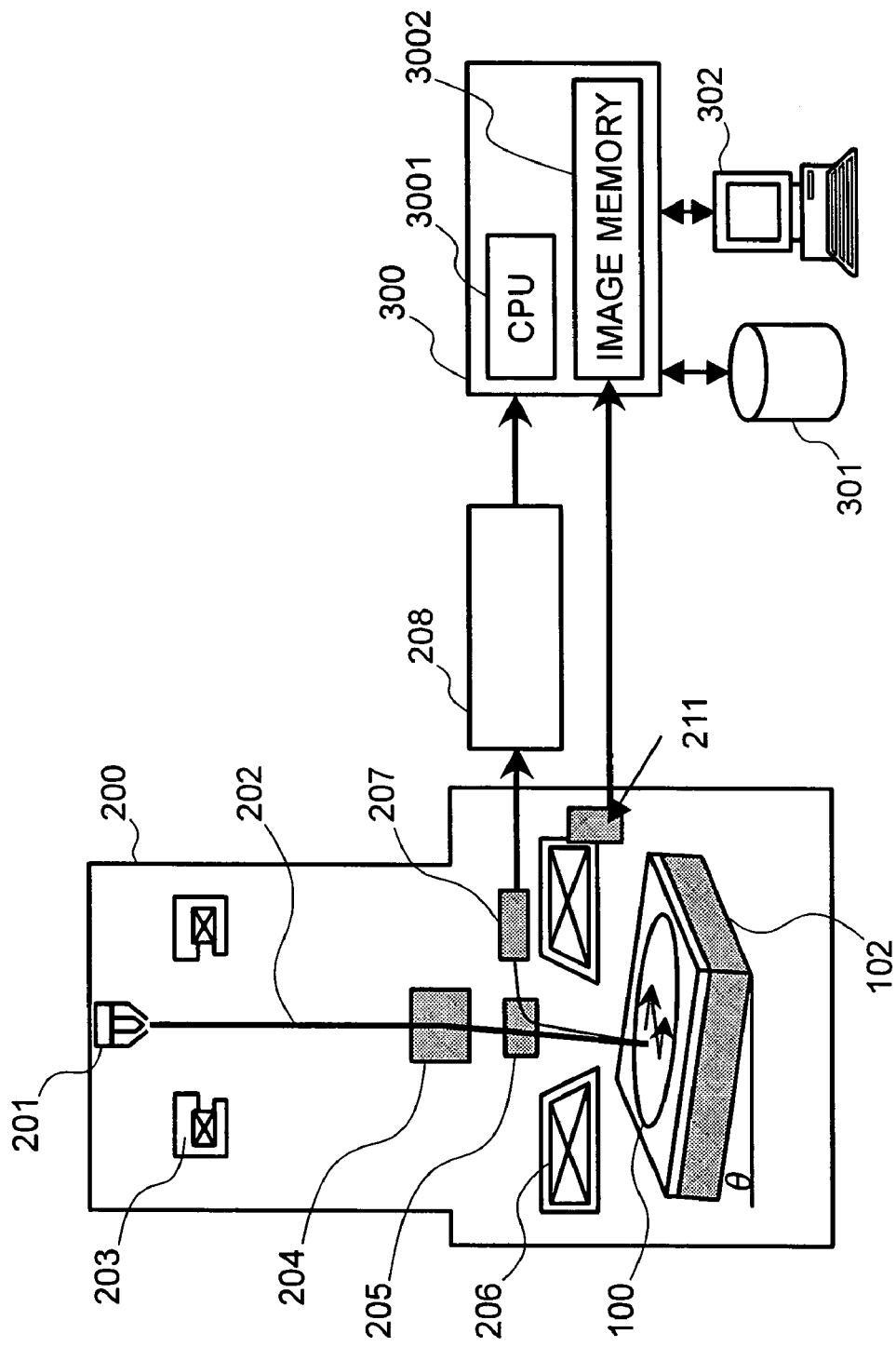
FIG. 19 is a front view illustrating a schematic configuration of an evaluation system according to an eighth embodiment.

As shown in FIG. 19, a CD-SEM employed in the present embodiment is identical to one described in FIG. 9 in basic configuration but different from the configuration shown in FIG. 9 in that a tilt stage 102 is provided which is movable within an XY plane and has a tilt function. Owing to the provision of the tilt stage 102, a tilt image can be obtained in addition to the normal top-down view image.

In the tilt image, a portion equivalent to the left resist sidewall increases in the number of pixels, and a portion equivalent to the right resist sidewall decreases in the number of pixels (where the tilt of the tilt stage is directed to the upper right with respect to a sample as shown in FIG. 19). Attention in the present embodiment is directed toward a line profile of the sidewall equivalent portion on the side of the increase in the number of pixels.

Figure 20A:
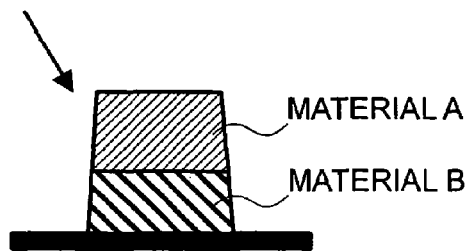
FIG. 20A is a cross-sectional view of a pattern, showing a method for acquiring a tilt image, which is employed in the eighth embodiment.
Figure 20B:
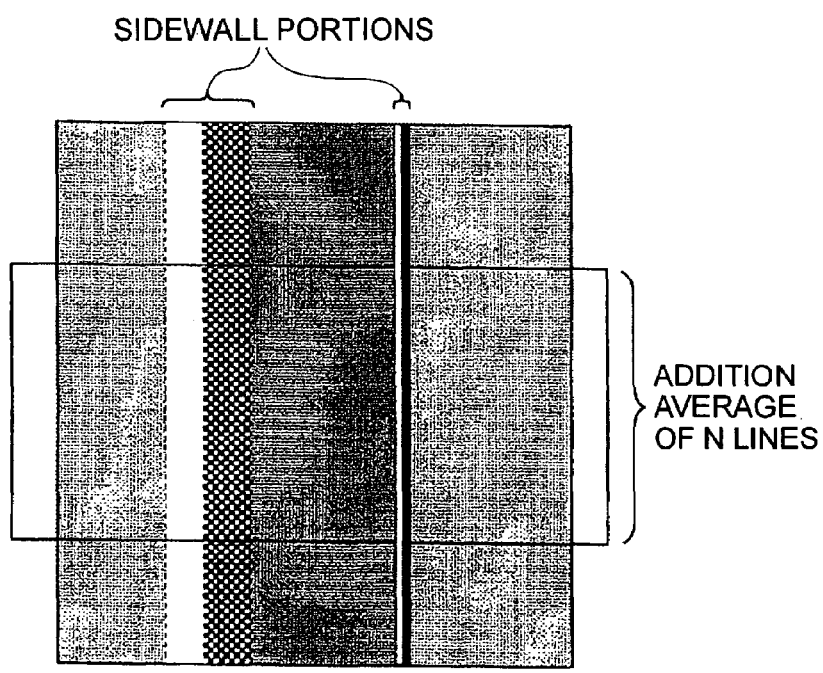
FIG. 20B shows an SEM tilt image acquired by the method shown in FIG. 20A.
Figure 20C:
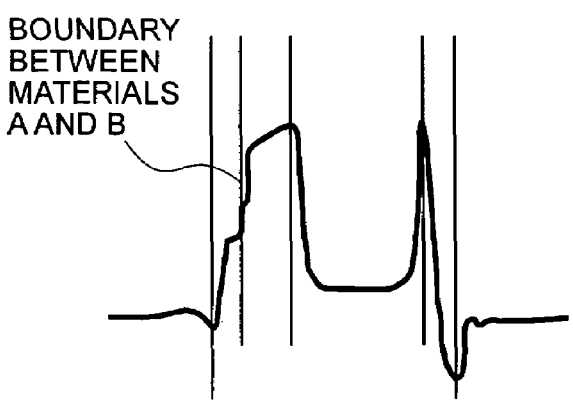
FIG. 20C is a signal waveform diagram of the tilt image shown in FIG. 20B.

Since the influence of the edge effect and beam resolution can be avoided if the inclined plane of the stage can be detected in a sufficient breadth, more detailed information about the sidewalls can be obtained. In the case of the multilayer film, in particular, wherein the different types of films of the polysilicide gate or the like shown in FIG. 3B are multilayered, the top-down view image is low in the number of pixels equivalent to the sidewall portion. Therefore, it is difficult to detect its boundary position. However, when an electron beam is applied from the direction diagonal to the corresponding pattern as in the direction indicated by arrow in FIG. 20A, such an SEM image (tilt image) as shown in FIG. 20B is obtained. A line profile at this time is represented as shown in FIG. 20C. If such a tilt image as shown in FIG. 20B is used, then the boundary can easily be detected. If the boundary position of the multilayer film can be detected, then the dimensions of a target sample for every portion thereof can be measured in isolation even in the case of the sidewall shape near the verticality as in the gate pattern shown in FIG. 3B and an inverse taper.

In the present embodiment, it is also feasible to acquire a plurality of images different in tilt angle, which are already known in angle, inclusive of the top-down view, and calculate the height of the pattern, based on the principle of stereo vision. Although the three-dimensional form has been estimated from the pattern height of the structure model data in the sixth embodiment, a sectional shape and/or three-dimensional form based on actual height information can be estimated if the height can be estimated from the stereo vision.

Incidentally, it is needless to say that the column of an electron optical system may be tilted in place of tilting of the stage, or the deflection angle of an irradiated electron beam may be varied to change the angle thereof incident on the sample.

The sectional shape and/or three-dimensional form evaluations according to the present embodiment may be used in combination with the first through seventh embodiments. In this case, the number of pixels equivalent to each of the sidewall portions increases owing to the use of the tilt image and hence higher accuracy form information is obtained and by extension, more accurate evaluations are made possible, in addition to effects similar to those described in the embodiments shown up to now. Further, it is also possible to measure an inverse taper and a pattern having vertical sidewalls, which are unmeasurable upon the use of top-down view alone.

Figure 21:
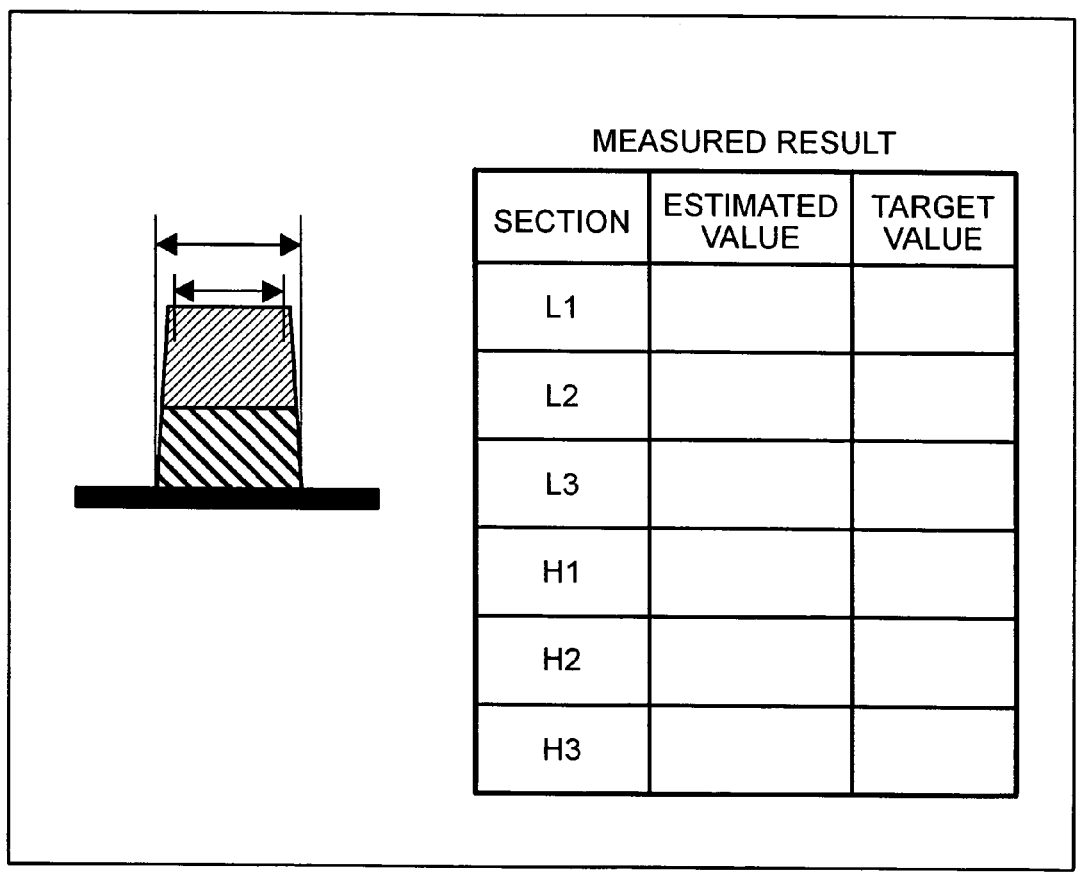
FIG. 21 is a front view of an output screen showing the result of detection obtained in the eighth embodiment.

FIG. 21 shows an example of the output of a result obtained by the present embodiment. Since the more accurate sectional shape based on actual measurement can be determined in the present embodiment, a sectional shape estimated from the actual result of measurement and length-measuring values of designated respective portions are displayed on the output screen. At this time, target dimensional values of respective portions of a target pattern sectional shape can be displayed on the same screen.

Ninth Embodiment

A ninth embodiment will be explained using FIGS. 22 and 23. While the first through seventh embodiments have described the case in which only the SEM image observed from the upper surface is used, and the eighth embodiment has described the case in which the tilt images are combined, the ninth embodiment will explain a method using reflected electron images.

Figure 22:
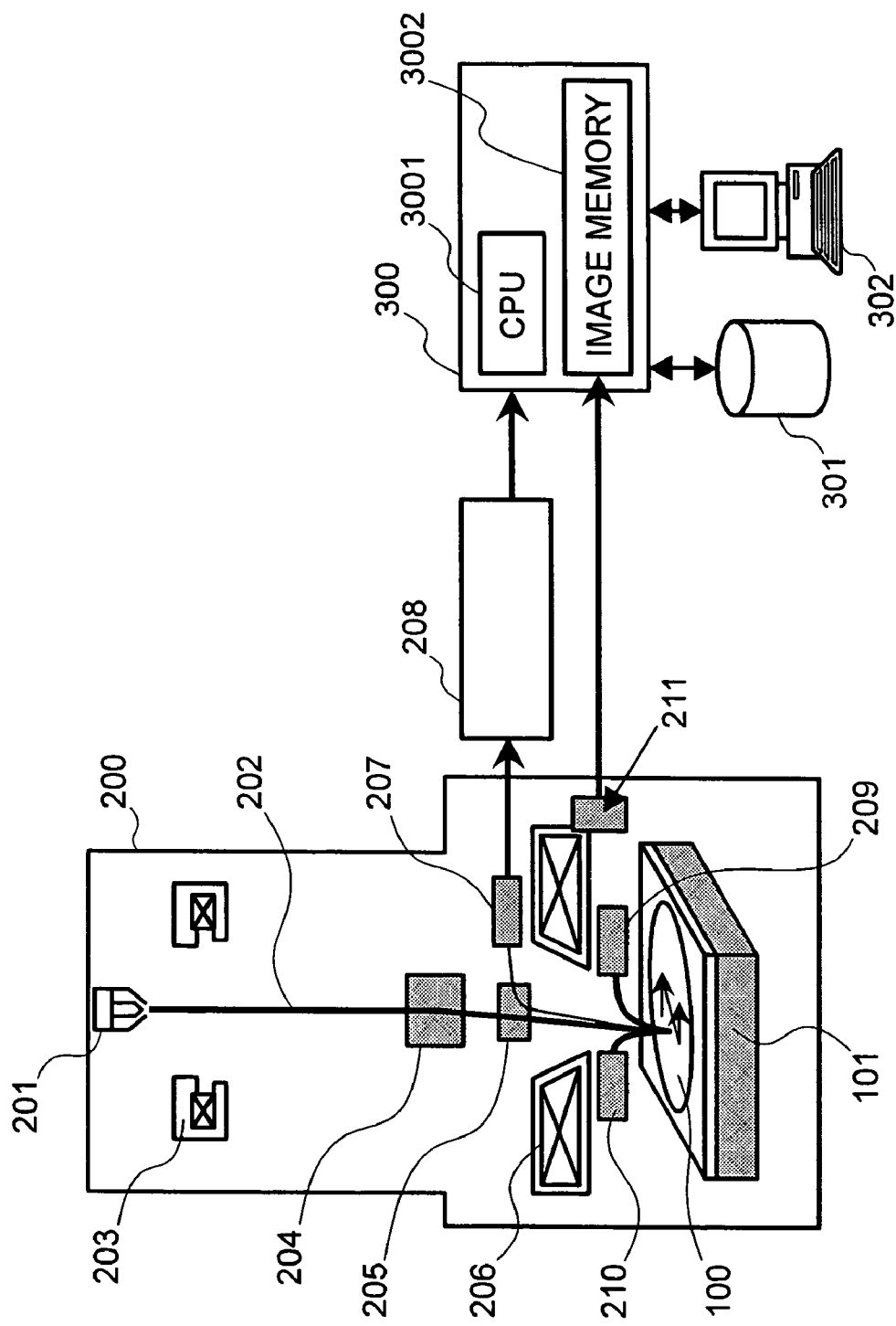
FIG. 22 is a front view showing a schematic configuration of an evaluation system according to a ninth embodiment.

A CD-SEM employed in the present embodiment has such a configuration as shown in FIG. 22. The present CD-SEM is different in configuration from the CD-SEM shown in FIG. 9 in that reflected electron detectors 209 and 210 are further provided. Thus, such reflected electron images (shadow images) as shown in FIGS. 23A and 23B can be obtained owing to further provision of the reflected electron detectors 209 and 210 in addition to the normal top-down view image obtained by the normal secondary electron detection using a secondary electron detector 207. Since the reflected electron images are capable of obtaining signals dependent on the plane direction as viewed on the surface of a target, a tilt angle of the surface of the sample can be estimated by the difference in signal amount between points that correspond to each other between such two images as shown in FIGS. 23A and 23B. If surface tilt angles at the respective points are estimated and integrated, then information about the height of the sample surface can also be obtained.

It is generally known that each of the reflected electron images depends on the atomic number of an object and changes in signal amount. The reflected electron images highly depend on the quality of material. Therefore, as shown in FIGS. 3B and 3E, measurements higher in accuracy than those by the secondary electron can be made on the pattern formed by combination of the different materials through the use of the reflected electron images. In a manner similar to the eighth embodiment, the pattern dimensional measurement may be carried out using the tilt images of reflected electrons. By using the present embodiment in combination with the first through seventh embodiments, the evaluation of a material's boundary portion becomes easy and hence a more accurate pattern evaluation is enabled.

If the three-dimensional form evaluation according to the present embodiment is used in combination with the first through seventh embodiments, then the boundary face between the different types of materials can definitely be discriminated. Therefore, higher accuracy form information is obtained and by extension, a more accurate evaluation is made possible.

Tenth Embodiment

The ninth embodiment has described the measuring means using the reflected electron images. Both the secondary electron image and reflected electron images described in the embodiments illustrated till now change in material and form dependence according to the conditions (accelerating voltage and current of beam, the potential of wafer, etc.) of an electron optical system. Therefore, a tenth embodiment will explain a means for optimizing these conditions for the electron optical system.

Figure 24:
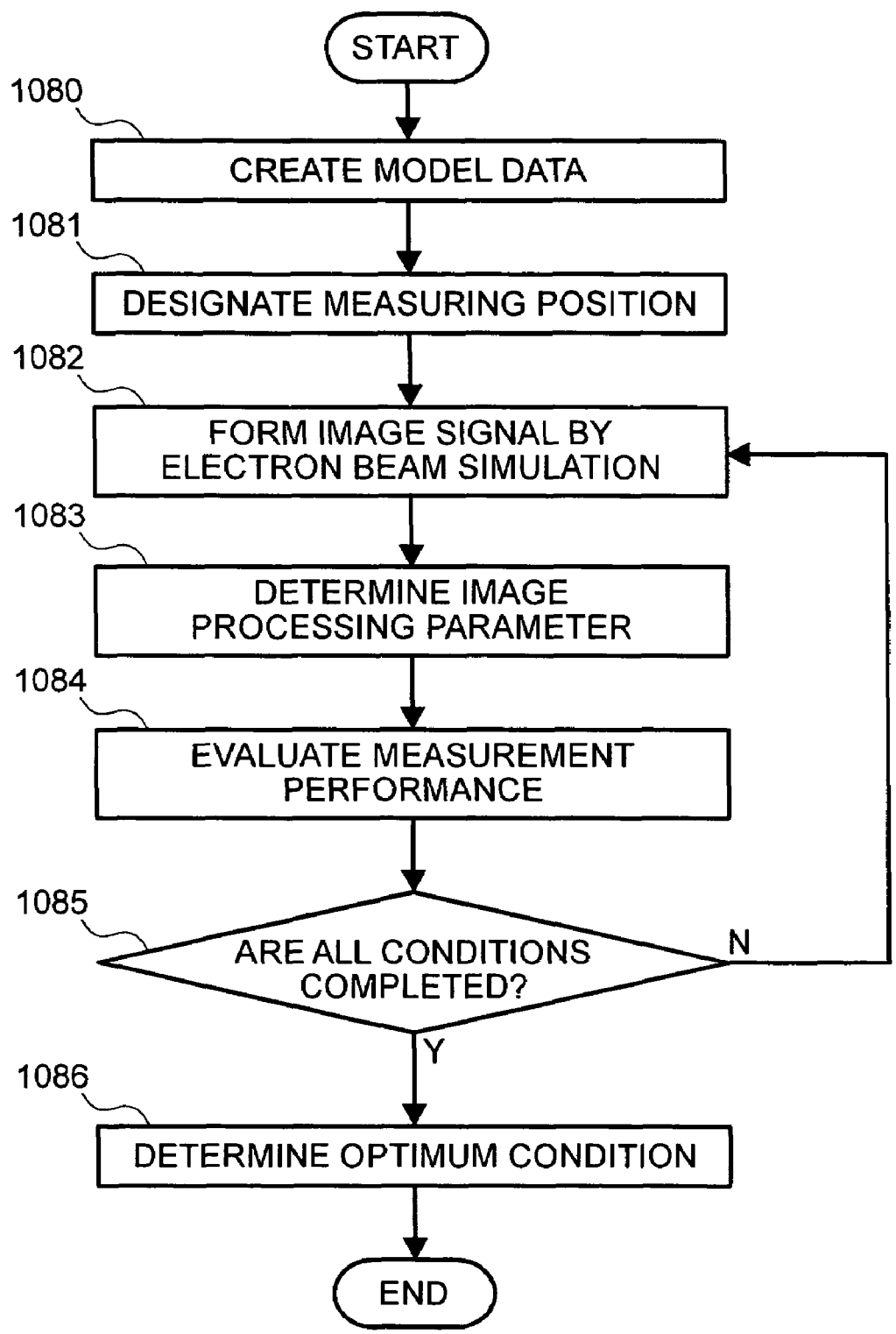
FIG. 24 is a flow diagram showing an image acquisition condition setting procedure according to a tenth embodiment.

FIG. 24 is a flow of the tenth embodiment. In a manner similar to the third embodiment, model data intended for evaluation is first created (Step 1080). Next, a desired measuring position is designated (Step 1081). At this time, a plurality of measuring positions may be designated if necessary. Next, simulation is performed on combinations of image acquisition conditions (beam accelerating voltage, current, wafer potential, magnification, tilt angle, etc.) settable to the model data by a device to thereby generate a simulation electron beam image (Step 1082). Typical combinations are registered in advance and the image acquisition conditions may be selected out of them.

Next, an image processing parameter for measuring a desired measuring position is determined with respect to the resultant simulation image by the method described in the first embodiment (Step 1083). An error between the obtained measured value and an actual dimensional value (which is assumed to be the known value because of simulation) is evaluated (Step 1084). Steps 1082 through 1084 are performed on all designated image acquisition conditions. When the processing for all the conditions is terminated, the image acquisition condition under which the error evaluated at Step 1084 is minimized can be determined as the optimum condition. When a plurality of measuring points exist at this time, for example, a process for selecting an image acquisition condition under which the average of errors measured at all points is small, may be performed.

If the sectional shape and/or three-dimensional form evaluations according to the present embodiment are used in combination with the first through seventh embodiments, then the optimum image acquisition condition and image processing condition can be easily determined according to the structure of the target sample and the desired measuring point. As a result, the present embodiment also has the advantage that an improvement in measurement accuracy and an improvement in reliability of the measured result can be achieved.

Eleventh Embodiment

Figure 25:
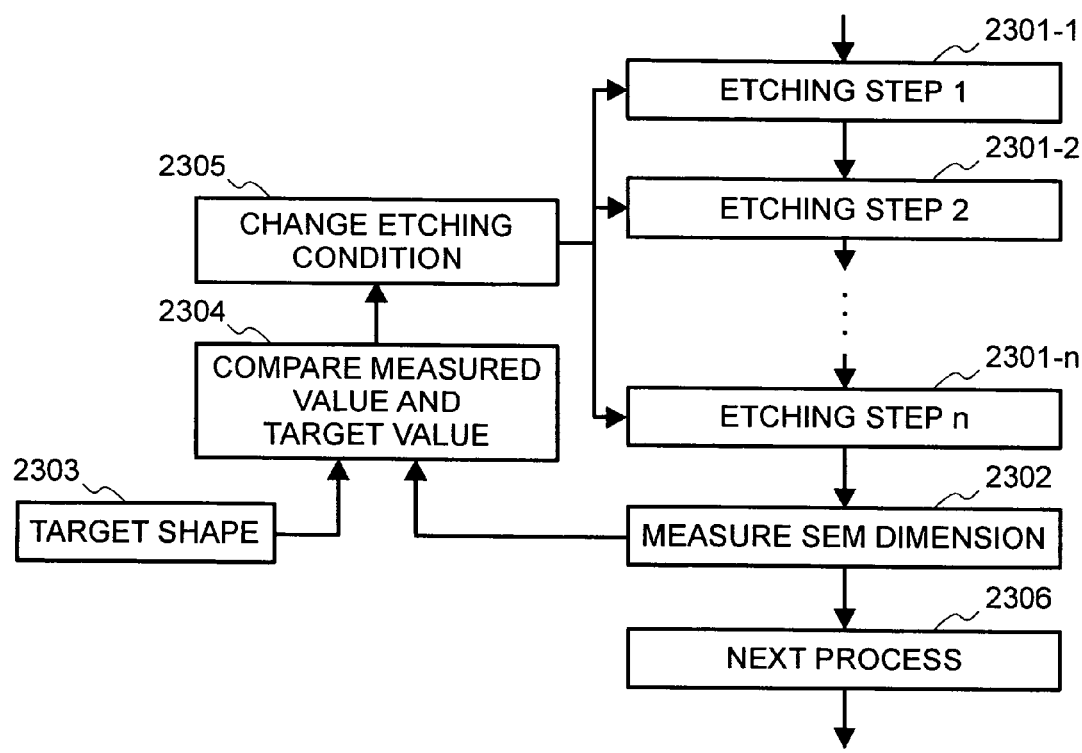
FIG. 25 is a flow diagram illustrating a semiconductor process control method according to an eleventh embodiment.

According to the embodiments described so far, the dimensions of the designated point can be measured easily and properly even in the case of patterns complex in structure. Thus, if a complex shape can be evaluated properly, then an etching condition can be optimized with its result as the base. As shown in FIG. 25, an etching process generally comprises a plurality of steps 2301-1 through 2301-*n*. If the pattern form of a sample is of such a structure as shown in FIG. 12A, for example, then respective steps for at least Si etching, $SiO_2$ etching, $Si_3N_4$ etching and $SiO_2$ (hard mask) etching are needed. The conditions for an etching device are adjusted every their steps and processing is carried out.

Thus, if the etching processing condition is changed with the difference between a dimension evaluation result at each point, which is obtained by measurement of an SEM, and a target shape as the base as shown in FIG. 24, then a desired pattern can be always formed. At this time, a sectional shape and/or three-dimensional form of a pattern can be estimated by acquiring a plurality of tilt images based on such a stage tilt or beam tilt or lens-barrel tilt or the like as described in the eighth embodiment and image-processing them. Data of respective portions of the resultant sectional shape and/or three-dimensional form are compared with a target dimension, so that the state of etching processing can be evaluated. Using the pattern evaluation system of the present invention in this way makes it possible to always maintain a satisfactory pattern processed form and prevent making up of a defective product.

Figure 26:
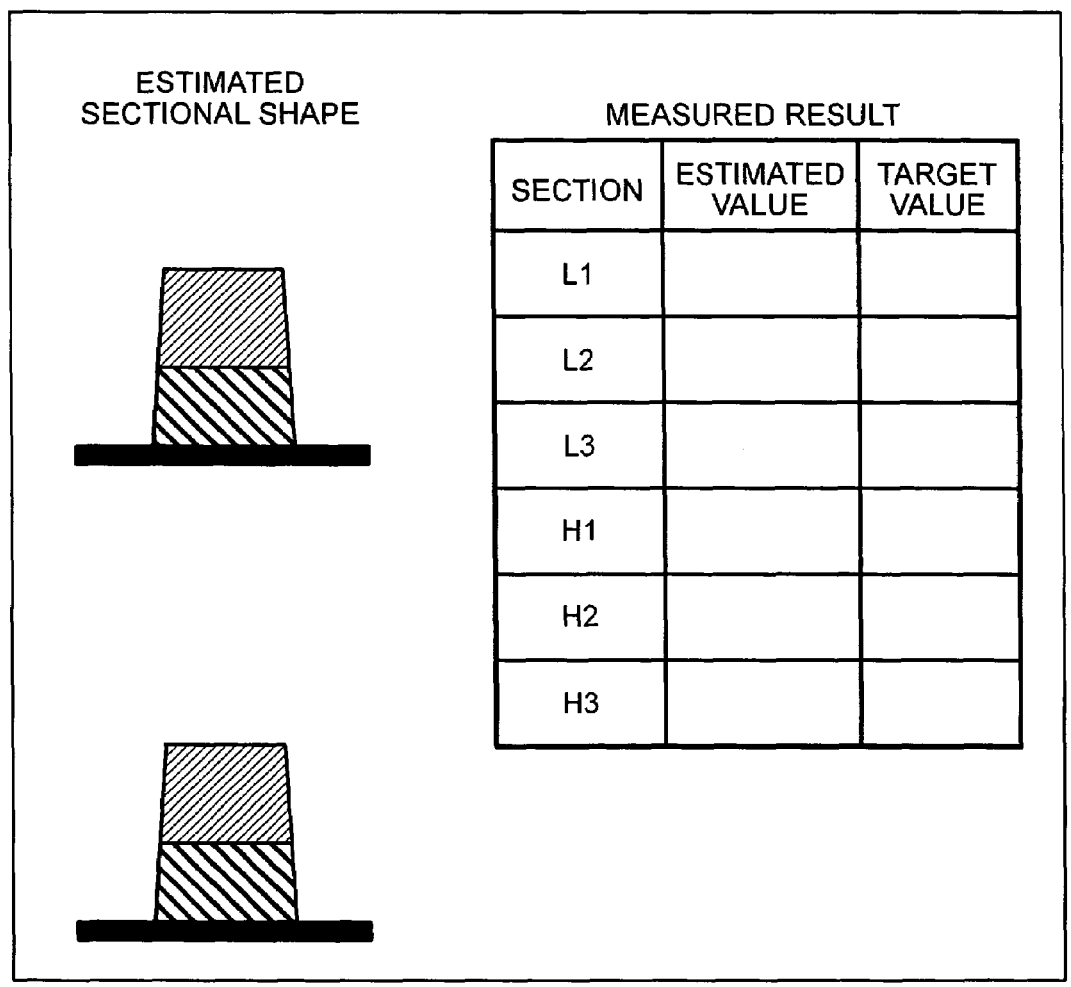
FIG. 26 is a front view of an output screen showing the result of detection obtained in the eleventh embodiment.

FIG. 26 shows one example of the output of the present embodiment. In the present embodiment, the pattern's sectional shapes estimated based on actual measurements and target shapes are outputted in a visually comparable form. That is, according to the present invention, the pattern's sectional shapes estimated as a result of measurement and the dimensions of designated respective portions, and their corresponding target shapes, target dimensions of the respective portions and their allowable error ranges are displayed on the same screen.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for measuring dimensions of a pattern, comprising the steps of:

applying a focused electron beam onto a sample with a pattern formed in a surface thereof and scanning the sample to acquire a secondary electron image on the sample surface including the pattern, and displaying the secondary electron image on a screen;

setting a pair of regions for performing image processing on the displayed secondary electron image;

processing the secondary electron image within the set pair of regions by changing an image processing condition, thereby extracting characteristic points from the secondary electron image in each of the pair regions;

storing an image processing condition corresponding to the extracted characteristic points; and processing the secondary electron image of the sample using the stored image processing condition to measure the dimensions of the pattern by calculating a distance between the extracted characteristic points in each of the pair of regions.

2. The method according to claim 1, wherein in the step of extracting the points characterized in the secondary electron image, a desired point on the secondary electron image is designated within the set pair of regions, and the secondary electron image placed at the designated desired point and lying in a region close thereto is processed while an image processing condition is being changed, thereby extracting points characterized in the secondary electron image.

3. The method according to claim 1, wherein in the step for extracting the points characterized in the secondary electron image, the secondary electron image is processed while an image processing condition is being changed, thereby to detect points characterized on the secondary electron image within the set pair of regions, and the detected characterized points on image signal are displayed on the screen with being superimposed on the secondary electron beam image, and a desired characterized point is extracted from the characterized points displayed on the secondary electron image in superimposed form.

4. The method according to claim 1, wherein the secondary electron image of the pattern includes a tilt image.

5. The method according to claim 4, wherein information about the height of the pattern intended for evaluation is obtained based on the tilt image.

6. A method for measuring dimensions of a pattern, comprising the steps of:

creating structure data of a pattern intended for evaluation;

designating a measuring point on the created structure data;

generating a simulation electron beam signal of the created structure data;

detecting points characterized in an image signal around the designated measuring point in the generated simulation electron beam signal;

selecting a point closest to the designated measuring point from the detected points characterized in the image signal;

setting an image processing condition under which the selected point characterized in the image signal has been detected, as a pattern measuring condition;

imaging a pattern identical in shape to the evaluation-targeted pattern formed on a sample under an electron microscope to acquire a secondary electron image; and processing the picked-up secondary electron image using the set pattern measuring condition to thereby measure dimensions of the pattern.

7. The method according to claim 6, wherein in the step for generating the simulation electron beam signal of the created structure data, the created structure data is corrected using actual section image data of the pattern intended for evaluation, and a simulation electron beam signal is generated using the corrected structure data.

8. The method according to claim 6, wherein any of points showing a local maximum value and a local minimum value of the image signal, a local maximum value and a local minimum value of a primary differential signal, and points that intersect at zero is used as each of the points characterized in the image signal.

9. The method according to claim 6, further including the step of displaying on the screen, the created structure data and a point on the structure data, corresponding to the selected point characterized in image signal.

10. The method according to claim 6, wherein in the step of generating the simulation electron beam signal of the created structure data, a predetermined edge detecting process for dimensional measurement is effected on the simulation electron beam signal of the created structure data, and a point corresponding to an edge detection position detected by the edge detecting process is displayed on the screen so as to be superimposed on the structure data.

11. The method according to claim 6, wherein the secondary electron image of the pattern includes a tilt image.

12. The method according to claim 11, wherein information about the height of the pattern intended for evaluation is obtained based on the tilt image.

13. A method for measuring dimensions of a pattern, comprising the steps of:

creating structure data of a pattern intended for evaluation;

designating a measuring point on the created structure data;

generating a simulation electron beam signal of the created structure data;

performing an edge detecting process on the generated simulation electron beam signal in association with the designated measuring point and a region adjacent thereto to thereby detect a position of an edge;

storing a point on the structure data, corresponding to the detected edge position;

imaging a sample formed with a pattern identical in shape to the evaluation-targeted pattern under an electron microscope to acquire a secondary electron image of the pattern;

performing an edge detecting process on the acquired secondary electron image under the same condition as one for the simulation electron beam signal to thereby detect a position of an edge on the secondary electron image;

correcting the structure data using information about the detected edge position on the secondary electron image and information about the edge position on the structure data; and determining a sectional shape of the evaluation-targeted pattern, based on the corrected structure data and displaying the determined sectional shape of the evaluation-targeted pattern on a screen.

14. The method according to claim 13, wherein the sectional shape of the pattern intended for evaluation is displayed on the screen together with the secondary electron image.

15. The method according to claim 13, wherein in the step for creating the structure data of the pattern intended for evaluation, information about the height of the structure data of the pattern intended for evaluation is obtained from either information obtained by measuring the thickness of a film constituting the pattern intended for evaluation or information obtained by directly measuring the height of the pattern intended for evaluation or information about the specifications of a deposited film.

16. The method according to claim 13, wherein the secondary electron image of the pattern includes a tilt image.

17. The method according to claim 16, wherein the information about the height of the pattern intended for evaluation is obtained based on the tilt image.

18. A method for measuring dimensions of a pattern, comprising the steps of:

creating structure data of a pattern intended for evaluation;

designating a desired measuring point on the created structure data;

generating a plurality of simulation electron beam signals of the created structure data according to predetermined plural image generating conditions;

detecting points characterized in an image signal around the designated measuring point with respect to the generated plurality of simulation electron beam signals;

selecting a point closest to the designated desired measuring point from the detected points characterized in the image signal with respect to each of the plurality of simulation electron beam signals;

evaluating a difference between the desired measuring point and the point characterized in the image signal, closest to the selected desired measuring point with respect to each of the plurality of simulation electron beam signals;

selecting an image generating condition under which the difference is minimized, with respect to each of the plurality of simulation electron beam signals;

storing, as measuring conditions, the selected image generating condition and a condition for detecting the point characterized in image signal, closest to the desired measuring point with respect to an image generated on the selected image generating condition; and processing an image obtained by imaging a sample formed with a pattern identical in shape to the evaluation-targeted pattern under an electron microscope using the stored measuring conditions to thereby measure dimensions of the pattern.

* * * * *